US006891156B2

(12) United States Patent
DiCesare

(10) Patent No.: US 6,891,156 B2
(45) Date of Patent: May 10, 2005

(54) SAMPLE PLATE FOR MATRIX-ASSISTED LASER DESORPTION AND IONIZATION MASS SPECTROMETRY

(75) Inventor: Joseph L. DiCesare, Redding, CT (US)

(73) Assignee: Perkin Elmer Instruments LLC, Shelton, CT (US)

(*) Notice: Subject to any disclaimer, the term of this patent is extended or adjusted under 35 U.S.C. 154(b) by 36 days.

(21) Appl. No.: 10/426,599

(22) Filed: Apr. 30, 2003

(65) Prior Publication Data

US 2004/0217276 A1 Nov. 4, 2004

(51) Int. Cl.[7] .............................. B01D 59/44; C12Q 1/00
(52) U.S. Cl. ............................................. 250/288; 435/4
(58) Field of Search ................................. 250/282, 288, 250/364; 422/104, 102, 65, 63; 435/4

(56) References Cited

U.S. PATENT DOCUMENTS

| 4,676,274 | A |   | 6/1987 | Brown |
|---|---|---|---|---|
| 4,911,782 | A |   | 3/1990 | Brown |
| 5,200,152 | A |   | 4/1993 | Brown |
| 5,503,803 | A |   | 4/1996 | Brown |
| 5,853,894 | A |   | 12/1998 | Brown |
| 5,859,431 | A | * | 1/1999 | Cotrell et al. ................ 250/288 |
| 5,958,345 | A |   | 9/1999 | Turner et al. |
| 5,989,692 | A |   | 11/1999 | Brown |
| 6,037,168 | A |   | 3/2000 | Brown |
| 6,071,610 | A | * | 6/2000 | Jarrell et al. ................ 428/335 |
| 6,143,496 | A |   | 11/2000 | Brown et al. |
| 6,156,389 | A |   | 12/2000 | Brown et al. |
| 6,265,015 | B1 |   | 7/2001 | Brown |
| 6,287,872 | B1 | * | 9/2001 | Schurenberg et al. ........ 436/181 |
| 2003/0057368 | A1 | * | 3/2003 | Franzen et al. .............. 250/281 |
| 2003/0116707 | A1 | * | 6/2003 | Brown et al. ................ 250/288 |

OTHER PUBLICATIONS

Hung et al., Use of Poly (tetrafluoroethylene) as a Sample Support for the MALDI–TOF Analysis of DNA and Proteins, *Analytical Chemistry*, 71 (2), 518–521 (1999).

Strupat et al., 2,5–Dihydroxybenzoic acid: a new matrix for laser desorption—ionization mass spectrométry,. ABST *International Journal of Mass Spectrometry and Ion Processes*, vol. 111, 89–102 (1991).

Vallée et al., Orientation and nonlinear optical properties of N–4–nitrophenyl–(L)–prolinol crystals on nanosaturated poly (tetrafluoroethylene) substrates, *Journal of Chemical Physics*, vol. 115, No. 12, 5589–5596 (Sep. 2001).

Vestling et al., Poly (vinylidene difluoride) Membranes as the Interface between Laser Desorption Mass Spectometry, Gel Electrophoresis, and In Situ Proteolysis, *Analytical Chemistry*, 66, 471–477 (1994).

(Continued)

*Primary Examiner*—Nikita Wells
*Assistant Examiner*—James P. Hughes
(74) *Attorney, Agent, or Firm*—St. Onge Steward Johnston & Reens, LLC

(57) ABSTRACT

A sample plate for mass spectrometric analysis of a specimen is provided comprising a substrate having an electrically conductive surface, a mask applied to the electrically conductive surface. The mask is applied to the substrate with a rough surface to form at least one sample site. The sample site comprises a central portion formed from the electrically conductive surface and a marginal portion formed from the mask where the marginal portion is more hydrophobic than the central portion.

21 Claims, 36 Drawing Sheets

OTHER PUBLICATIONS

Blackledge et al., Polyethylene Membrane as a Sample Support for Direct Matrix–Assisted Laser Desorption/Ionization Mass Spectrometric Analysis of High Mass Proteins, *Analytical Chemistry,* 67, 843–848 (1995).

Guo et al., Improving the Performance of MALDI–TOF in Oligonucleotide Analysis Using SDIFA Technology, *Analytical Chemistry,* 72, 5792–5797 (2000).

Chen et al., Application of an Integrated Matrix–Assisted Laser Desorption/Ionization Time–of–Flight, Electrospray Ionization Mass Spectrometry and Tandem Mass Spectrometry Approach to Characterizing Complex Polyol Mixtures, *American Society for Mass Spectrometry,* (2001).

Hung et al., Use of Paraffin Wax Film in Maldi–TOF Analysis of DNA, *Analytical Chemistry,* 70 (14), 3088–3093 (1998).

Shen et al., Porous Silicon as a Versatile Platform for Laser Desorption/Ionization Mass Spectrometry, *Analytical Chemistry,* 73, 612–619 (2001).

Horneffer et al., Confocal laser scanning microscopy (CLSM) as a suitable imaging technique for studies of the analyte in MALDI preparations, *American Society for Mass Spectrometry*, (2000).

* cited by examiner

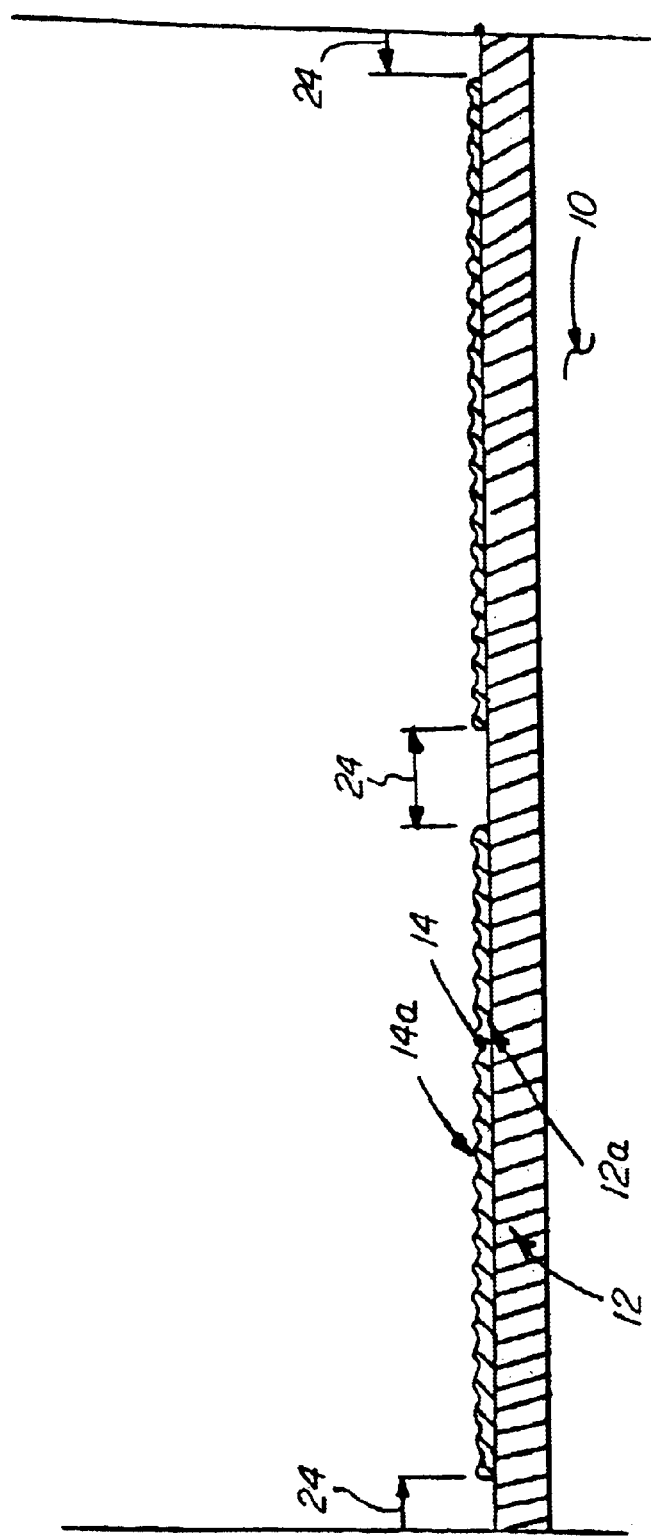

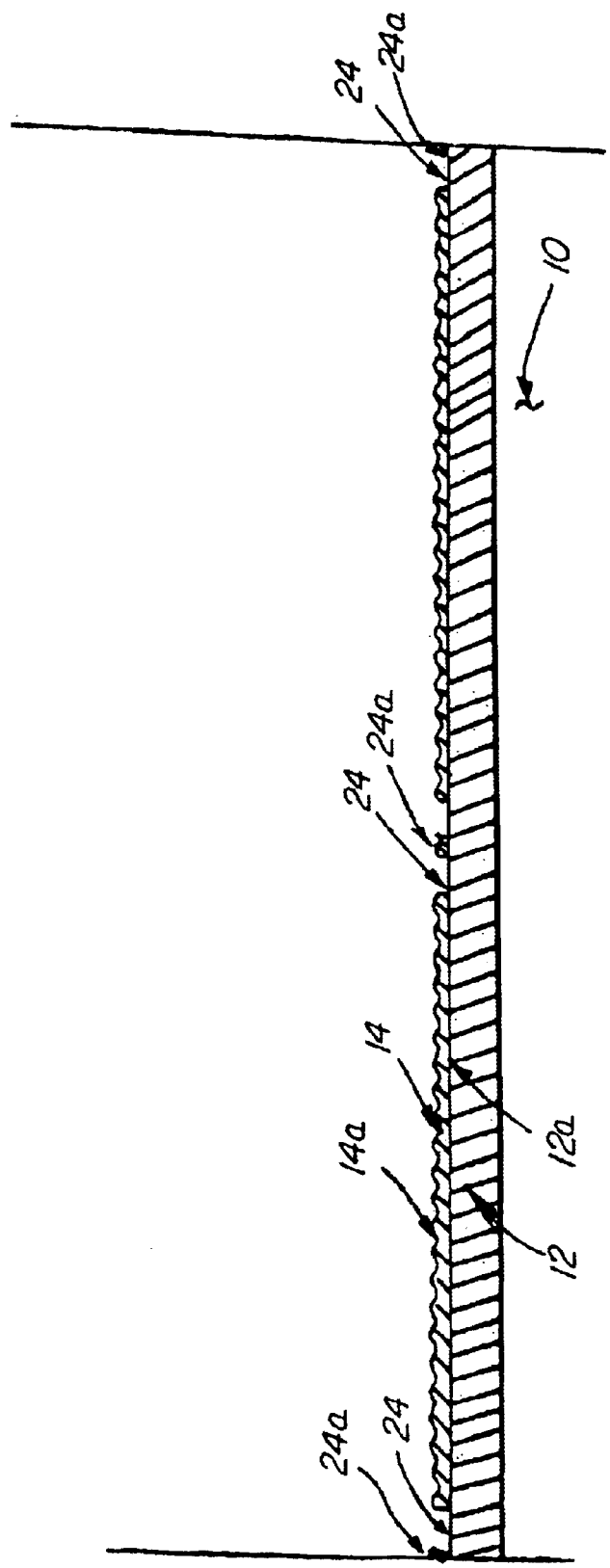

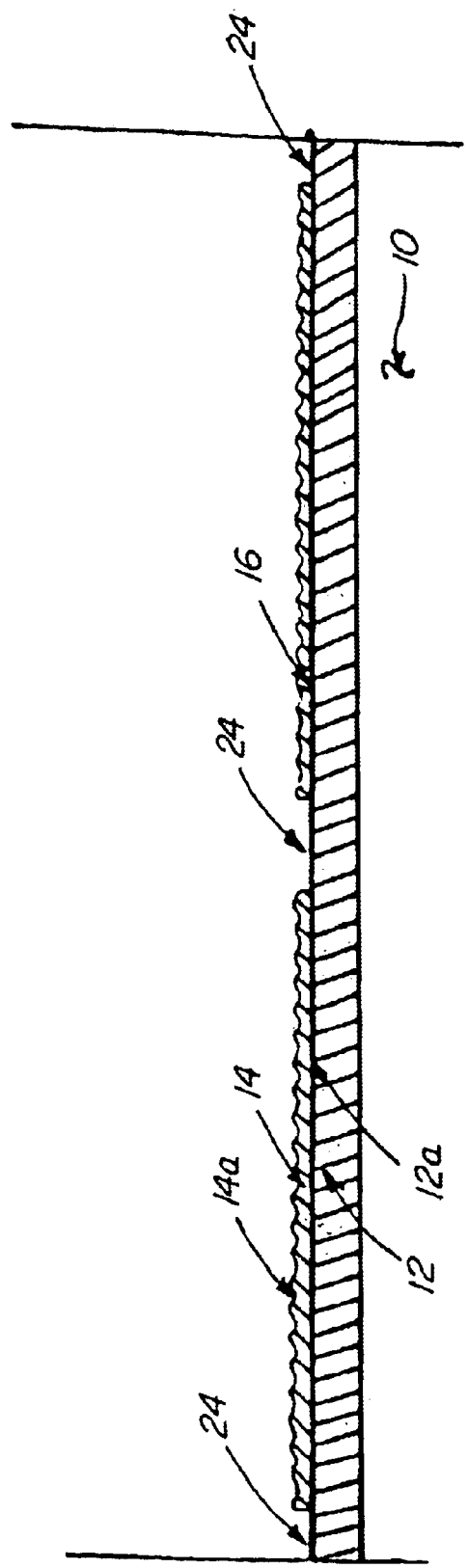

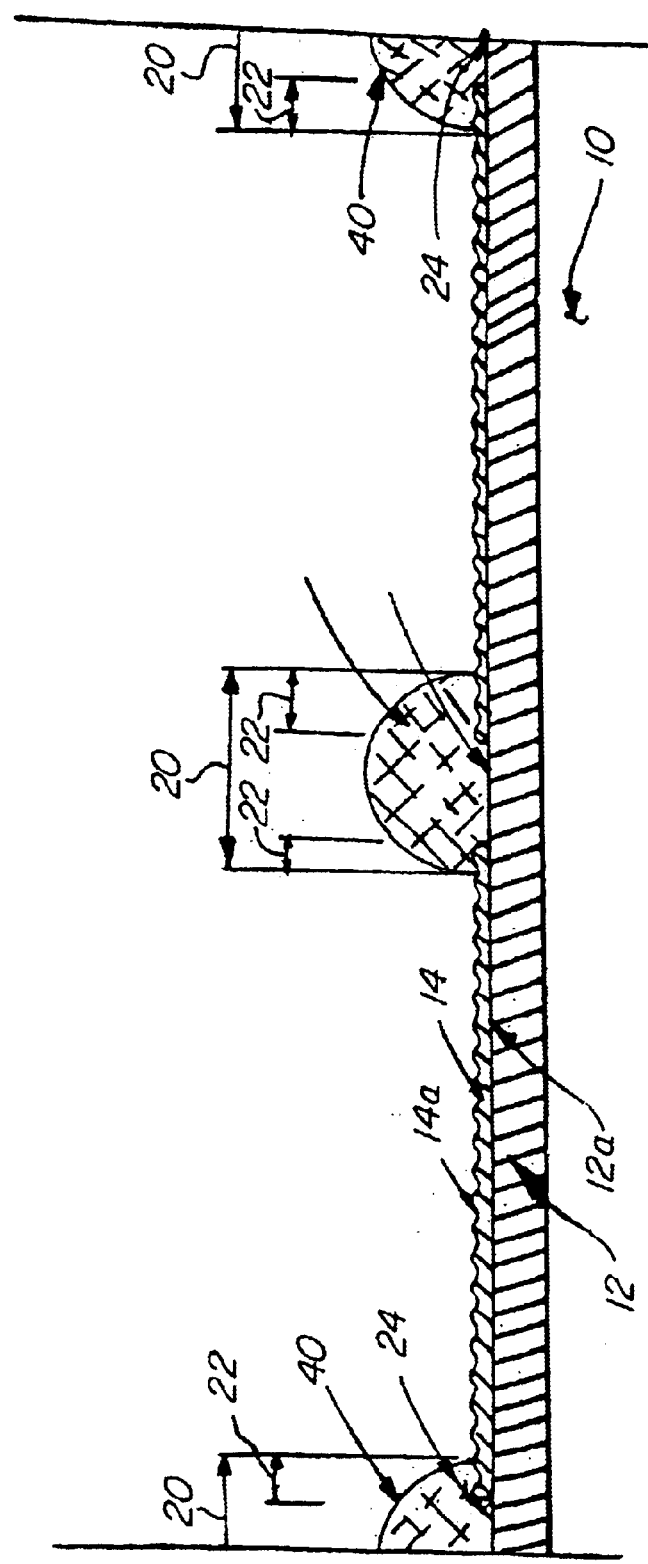

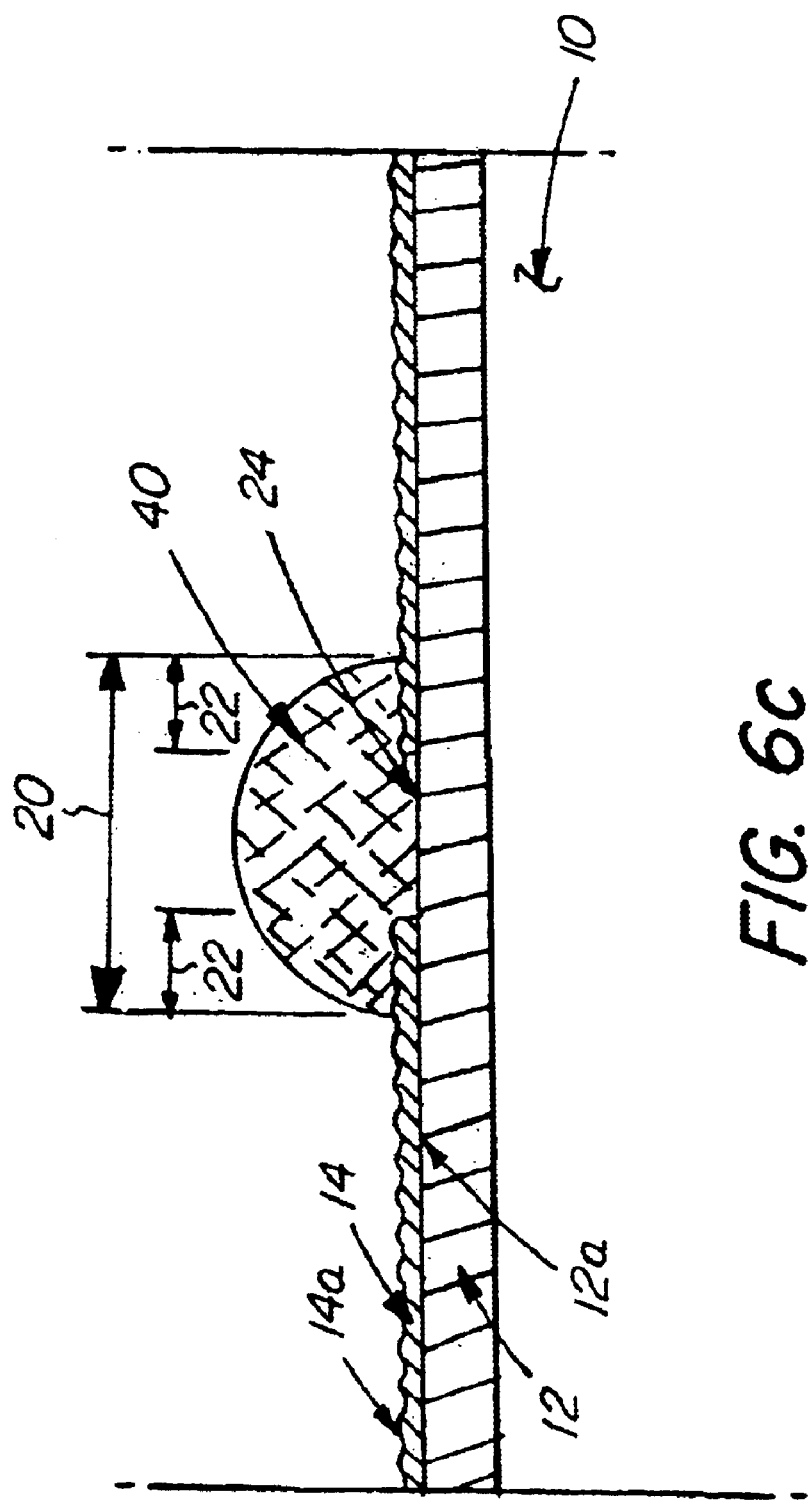

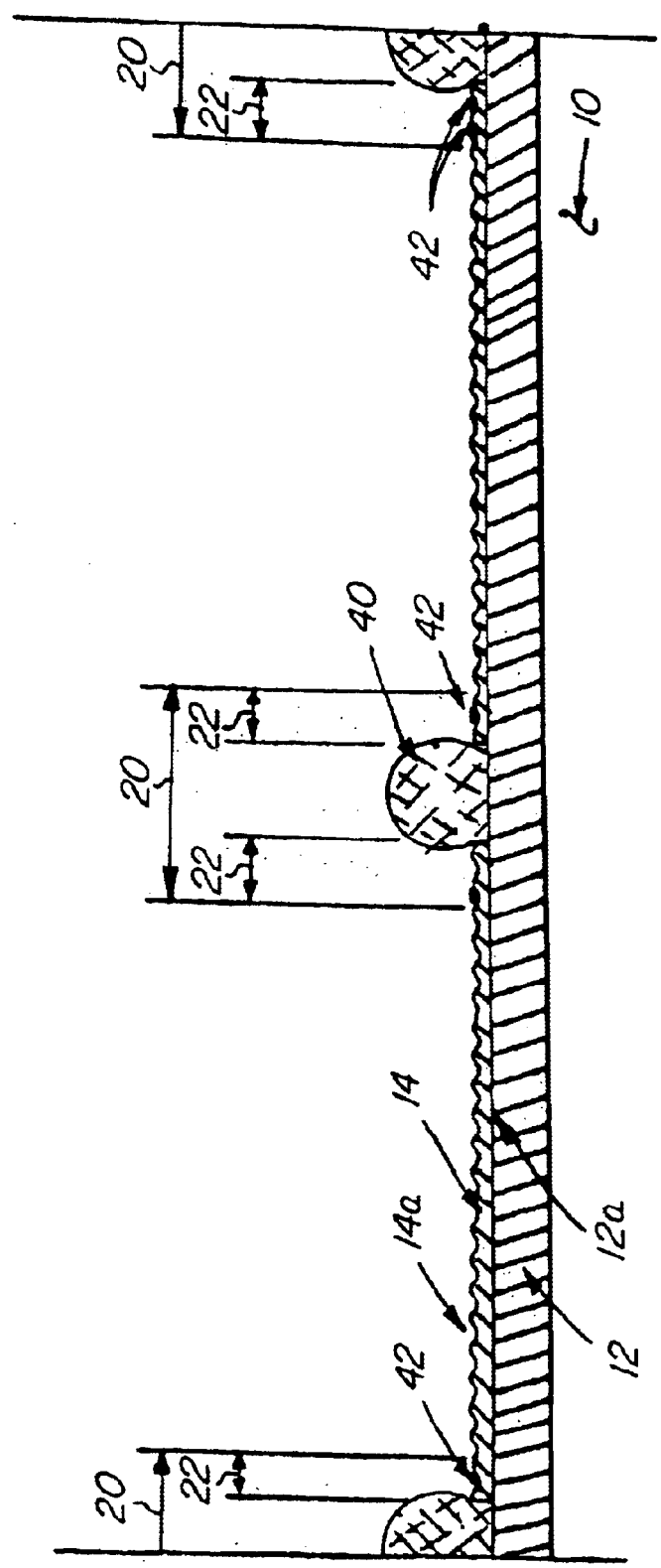

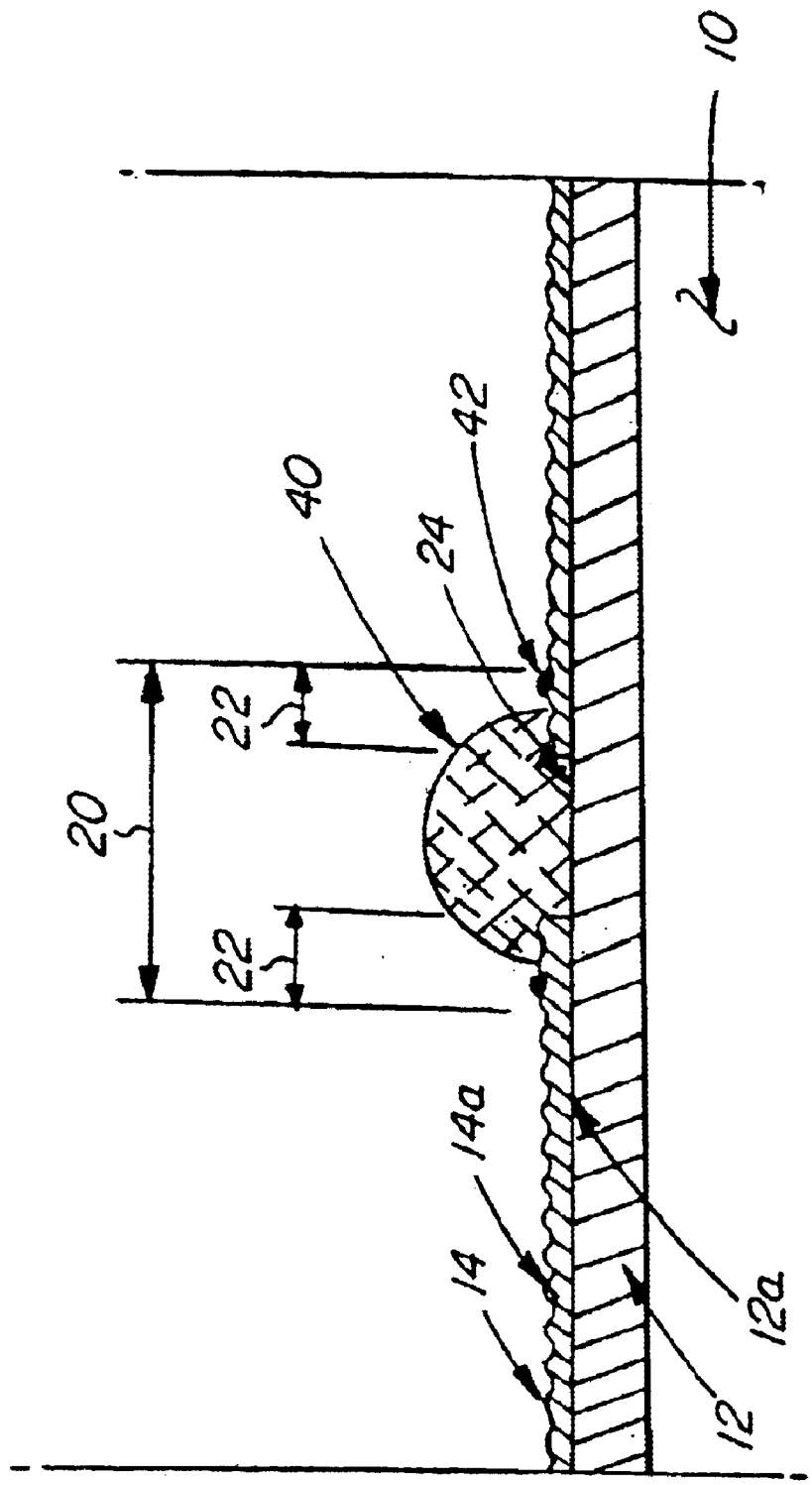

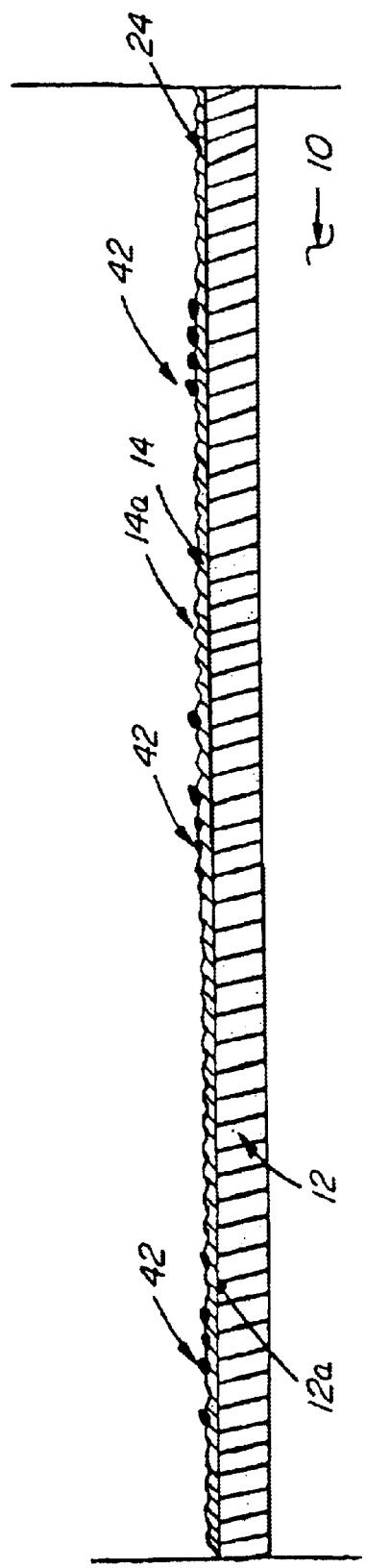

Black Teflon (matted appearance)

1 mg/ml CHCA; 1.5 ul

Gold/Black Teflon; 1.5 ul, 1 mg/ml, 30% ACN

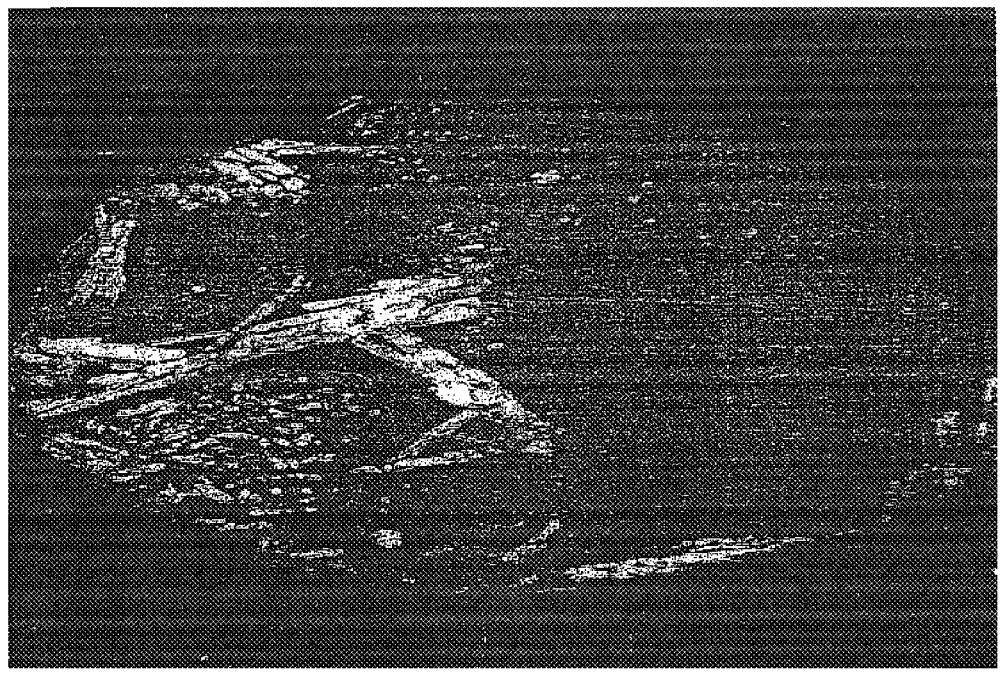
FIG. 19  DHB Crystals; 0.5 ul; >100 um

SAMPLE PLATE FOR MATRIX-ASSISTED LASER DESORPTION AND IONIZATION MASS SPECTROMETRY

FIELD OF THE INVENTION

The invention relates to a sample plate for use in mass spectrometry analysis of a specimen and a method of making same.

BACKGROUND OF THE INVENTION

Matrix-assisted laser desorption and ionization mass spectrometry (MALDI-MS) is an important analytical tool for the study and identification of biomolecules, particularly proteins, peptides, and nucleic acids such as DNA and RNA.

MALDI-MS results in a mass spectrum that graphically identifies biomolecules according to peaks that correspond to the biomolecules' concentration and mass. Using a library of known peaks, the biomolecules can be identified.

Various methods exist for the preparation of samples for analysis by MALDI-MS, including the dried droplet method. In the dried droplet method an aqueous sample containing the subject biomolecule is mixed with an organic compound, the matrix, which is usually suspended in an easily evaporative aqueous-organic solvent. The resulting liquid mixture containing the biomolecule, the matrix, aqueous solution, and solvents is referred to herein as the specimen.

The specimen is applied to the sample plate in a predetermined target area and allowed to dry. As the solvent begins to evaporate, and the biomolecule and matrix become more concentrated, the matrix molecules crystallize from solution while drying on the sample plate. The resulting crystals entrap the biomolecules on and/or within the crystals and in due course deposit on the sample plate.

Other methods of applying the specimen to the sample plate are also known. In the electrospray deposition method, the specimen is applied to the sample plate as a fine mist of microdroplets that evaporates very quickly forming the specimen crystals.

To analyze the biomolecules, the sample plate is inserted into the sampling compartment of a mass spectrometry instrument. A voltage is applied to the sample plate to permit the flow of electric current over the sample plate and prevent the possibility of an electrical charge buildup. To desorb the crystals, an ultra-violet (UV) laser scans the target area either by manual direction or in a predetermined automated fashion to irradiate the crystals. The laser beam radiation is absorbed by the matrix molecules, resulting in a vaporization of both the matrix molecules and the biomolecules. Once in the vapor phase, while still in close proximity to the target area, a charge transfer occurs as the matrix molecule loses a proton to the biomolecule. The ionized biomolecules are then drawn into the mass spectrometer where they are analyzed. Data processing yields a mass spectrum of a series of characteristic peaks corresponding to the biomolecules and matrix molecules. The signature of peaks is used to identify the biomolecules by reference to known peaks.

Prior art of interest includes U.S. Pat. No. 6,287,872 (herein incorporated by reference) relating to sample support plates for the mass spectrometric analysis of large molecules, such as biomolecules, methods for the manufacture of such sample support plates and methods for loading the sample support plates with samples of biomolecules from solutions together with matrix substance for the ionization of the biomolecules using matrix-assisted laser desorption (MALDI).

Also of interest is U.S. Pat. No. 5,958,345 (herein incorporated by reference) relating to a sample support for holding samples for use with an analysis instrument. The sample support is for use with analysis instruments, which rely on a beam of radiation or accelerated particles and a method for making the same. The holder includes a frame with one or more orifices covered by a support surface, typically in the form of a thin polymer film. The film is divided into hydrophobic and hydrophilic portions to isolate precise positions where samples can be placed to intersect a probe beam during analysis.

MALDI-MS performance suffers chiefly from analysis insensitivity. The sample plates that are used in MALDI-MS are typically metallic plates due to the need to apply a voltage across the plate. Known trays have a smooth hydrophilic surface where the applied specimen drop spreads over a relatively large area before drying and forming crystals. Consequently, to effectively irradiate the crystals the UV laser has to scan this enlarged area requiring extra time.

Another drawback of metallic plates is that they unfortunately often provide unsuitable results due to unintentional contamination from detergents. Since, metallic plates are also expensive, they are used repeatedly. Washing between each use may contaminate subsequent analysis.

It is known, that specimens are non-homogeneously distributed on and/or within the lattice that located at the specimen periphery. It is further known that some of these matrix crystals bear more biomolecules than others. Thus, as the laser covers a likely search area at the specimen periphery, it scans "sweet spots" having a comparatively higher specimen concentration in the matrices. When irradiated and detected, the sweet spots provide an inaccurate concentration reading of the biomolecule.

What is desired, therefore, is a sample plate for MALDI-MS analysis of a specimen wherein crystals are located in a sample site.

What is also desired is a durable and cost effective sample plate which enables archiving of samples.

What is also desired is a rough surface that is hydrophobic to enhance the formation of crystals in a sample site. What is further desired is a higher ratio of surface area to planar area of the hydrophobic mask.

SUMMARY OF THE INVENTION

Accordingly it is an object of the invention to provided a sample plate for mass spectrometry analysis of a specimen comprising a substrate having an electrically conductive surface; a mask selectively applied to the electrically conductive surface to produce a rough surface within a sample site, the sample site comprising a central portion formed from the electrically conductive surface and a marginal portion of the mask more hydrophobic than the central portion.

Another object of the invention is to provide a sample plate that overcomes known problems of analysis insensitivity.

A further object of the invention is to provide a sample plate wherein crystals are located at predetermined positions.

A still further object of the invention is to provide a durable and cost effective sample plate which enables archiving of samples.

These and other objects of the invention are achieved by providing a sample plate for mass spectrometry having a plurality of sample sites and a mask applied with a rough surface, the mask being more hydrophobic than the sample sites.

A sample plate for mass spectrometric analysis of a specimen is provided comprising a substrate having an electrically conductive surface, and a mask applied to the electrically conductive surface. The mask is applied to the substrate with a rough surface to form at least one sample site. The sample site comprises a central portion formed from the electrically conductive surface and a marginal portion formed from the mask where the marginal portion is more hydrophobic than the central portion.

BRIEF DESCRIPTION OF THE DRAWINGS

FIG. 3a is a cross-section at section B—B of FIG. 2a of a section of a circle sample plate in accordance with one embodiment of the invention.

FIG. 3c is an expanded elevation view of a circle sample site that includes a target area and a mask spot in accordance with one embodiment of the invention.

FIG. 4a is a cross-section at section B—B of FIG. 2a of a section of a circle sample plate with an electrically conductive coating applied to the substrate in accordance with one embodiment of the invention.

FIG. 6a is a cross-section at section C—C of FIG. 5a of a section of a circle sample plate in accordance with one embodiment of the invention wherein specimens have been applied on sample sites.

FIG. 6c is a cross-section at section D—D of FIG. 5b of a section of a channel sample plate in accordance with one embodiment of the invention wherein specimens have been applied on sample sites.

FIG. 8a is a cross-section at section E—E of FIG. 7a of a section of a circle sample plate in accordance with one embodiment of the invention wherein specimens of FIG. 6a have begun to dry.

FIG. 8c is a cross-section at section F—F of FIG. 7b of a section of a channel sample plate in accordance with one embodiment of the invention wherein specimens of FIG. 6b have begun to dry.

FIG. 10b is a cross-section at section G—G of FIG. 9b of a section of a channel sample plate in accordance with one embodiment of the invention wherein specimens of FIG. 6b have dried.

FIG. 17 is a photograph showing crystals that have crystallized around a sample target site in accordance with one embodiment of the present invention.

FIG. 19 is a photograph showing DHB crystals in target area having large surface area.

DETAILED DESCRIPTION OF THE DRAWINGS

FIGS. 1a, 2a, 3a, and 4a and FIGS. 1b, 2b, 3b, and 4b are views of a sample plate with at least one circular target area and rectangular target area, respectively, in accordance with one or more embodiments of the invention.

Figure 1A:
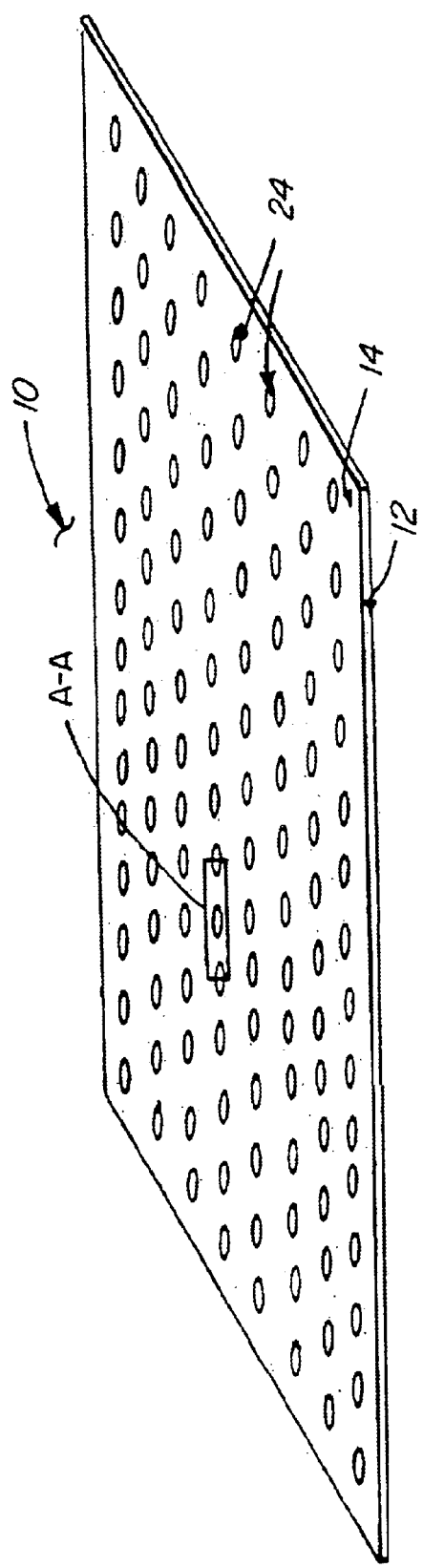
FIG. 1a is an isometric view of a sample plate with a circular target area in accordance with one embodiment of the invention.
Figure 1B:
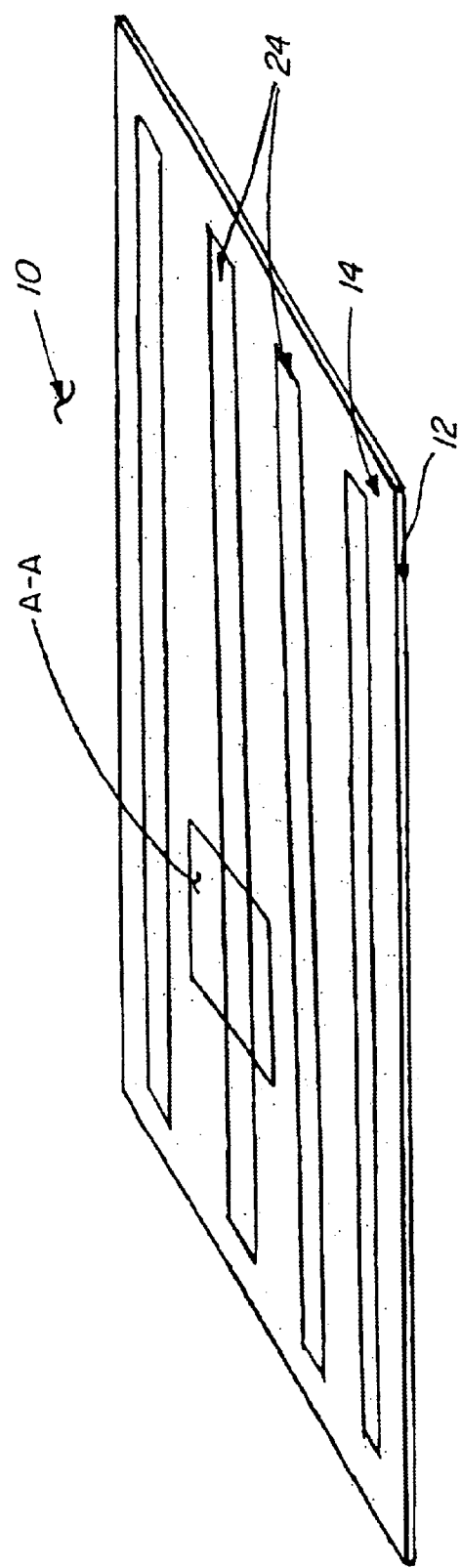
FIG. 1b is an isometric view of a sample plate with a rectangular target area in accordance with one embodiment of the invention.

Therein, FIGS. 1a and 1b are isometric views of sample plates with a circular target area and rectangular target area, respectively, in accordance with one or more embodiments of the invention. Sample plate 10 is characterized by any number of equally preferred embodiments of target area 24.

In one embodiment, referred to for simplicity as a circle sample plate 10, and depicted in FIG. 1a, sample plate 10 has a plurality of circular target areas 24. In the second embodiment, referred to for simplicity as a channel sample plate 10, and depicted in FIG. 1b, sample plate 10 has a plurality of rectangular, linear, and/or curvilinear target areas 24. Other embodiments, including combinations of geometries of target areas 24, are also contemplated.

Figure 2A:
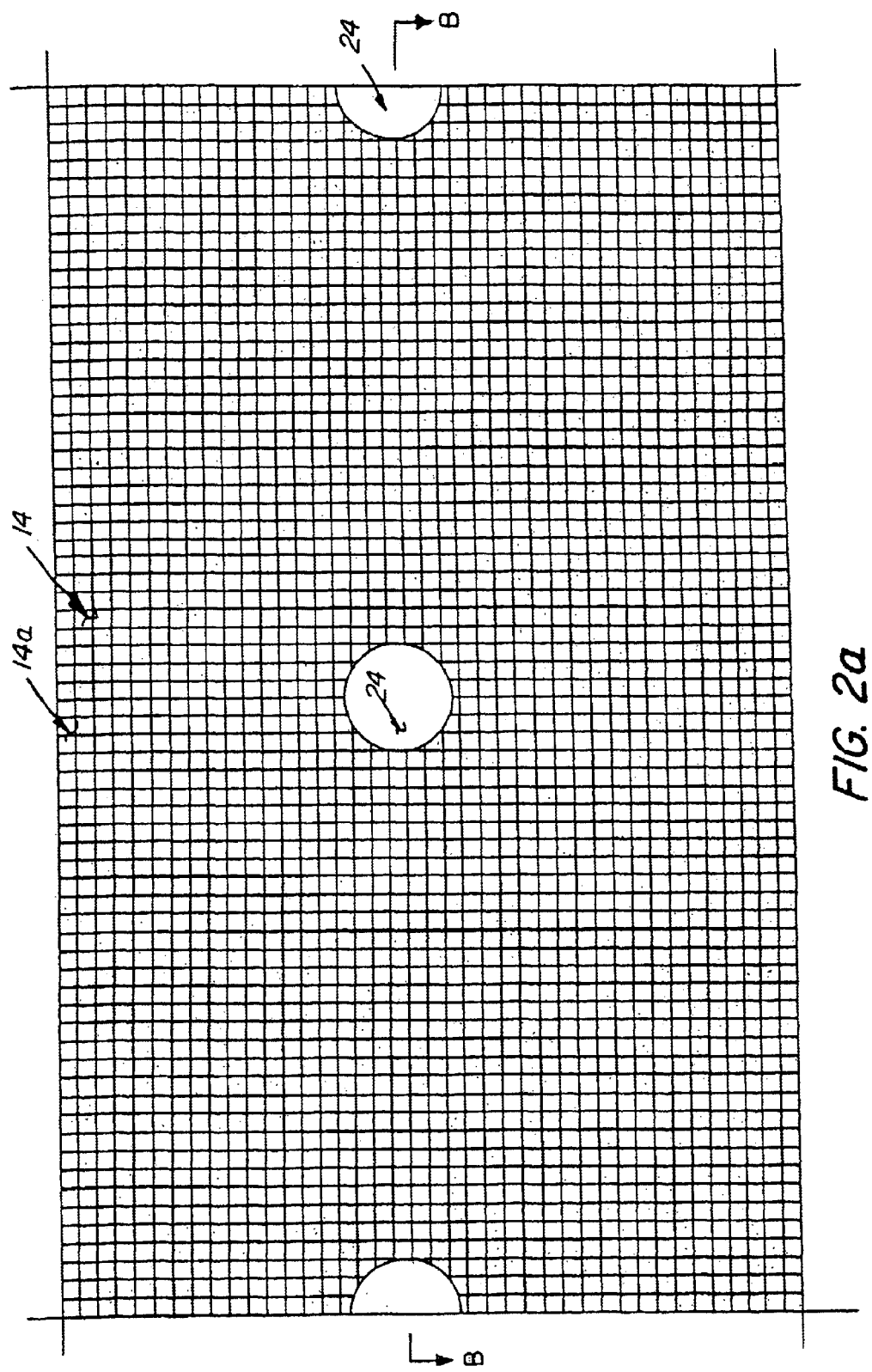
FIG. 2a is an enlarged view taken at area A—A of FIG. 1a of a section of a circle sample plate in accordance with one embodiment of the invention.
Figure 2B:
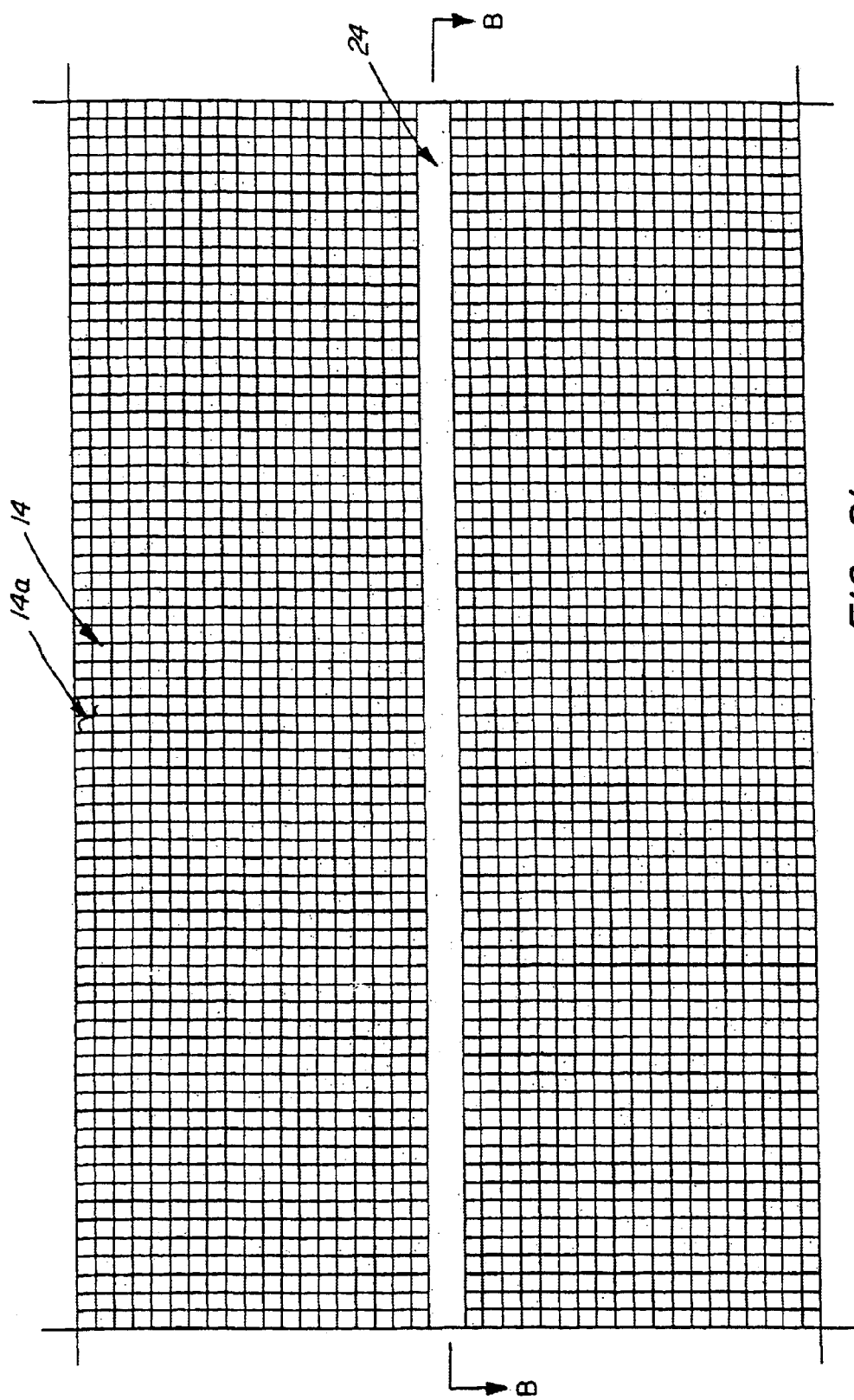
FIG. 2b is an enlarged view taken at area A—A of FIG. 1b of a section of a channel sample plate in accordance with one embodiment of the invention.

FIGS. 2a and 2b are enlarged views taken at area A—A of FIGS. 1a and 1b, respectively, of a section of a sample plate in accordance with one or more embodiments of the invention. FIGS. 3a and 4a and FIGS. 3b and 4b are cross-sections at section B—B of FIGS. 2a and 2b, respectively, of a section of a sample plate in accordance with one or more embodiments of the invention.

Sample plate 10 is a sample plate for applying a sample containing both matrix and biomolecules, referred to for convenience as specimen 40 (not shown for clarity in FIGS. 1a and 1b), for subsequent analysis in a mass spectrometry instrument within a sample site 20 (not shown for clarity in FIGS. 1a and 1b). Specimen 40 may be applied within sample site 20 by using the dried droplet method by spotting, i.e. in drop form, by streaking, i.e. in a continuous manner, by spraying, and/or any other form. Specimen 40 may also be applied within sample site 20 by the electrospray deposition method.

Sample plate 10 includes substrate 12 having electrically conductive surface 12a and mask 14 which is selectively applied to surface 12a to form a mask that has a rough surface 14a where at least one target area 24 is located within sample site 20, as will be explained further herein.

Sample plate 10 is sized appropriately for usage for biological laboratory processing using automated and/or manual processing equipment. Thus, sample plate 10 may be appropriately sized as microtiter plate size comprising a rectangular plan size of 116.2 mm by 83 mm and/or any other convenient size. Sample plate 10 may be any suitable thickness for automated and/or manual processing. In accordance with one embodiment of the invention sample plate 10 is at minimum 0.5 mm thick with a maximum planar variance of 50 $\mu$m or less. For clarity, herein, sample plate 10 is described in relation to a rectangular plan and generally planar shape of the plate. However, sample plate 10 may have any plan shape and/or may have non-planar shapes as are and/or may become appropriate for usage.

In accordance with one embodiment of the invention, sample plate 10 has an indicator, such as a notched corner, that aids in orienting sample plate 10. Other indicators may instead or in addition be a central notch; one or more physical, chemical, optical, and/or electromagnetic markers; and/or any other type of indicator or indicating and/or orienting means.

In accordance with one embodiment of the invention, sample plate 10 has a reference indicator for inventorying or archiving sample plate 10 before and/or after usage. Such an indicator may be a bar tag, alphanumeric reference, chemical and/or luminescent reference, and/or any indexing and/or archival reference that is readable by a machine and/or a human, attached to and/or integral with sample plate 10 on one or more of its surface.

In accordance with one embodiment of the invention, the reference indicator is sensitive to one or more wavelengths of the UV laser used in ionizing the crystals. Therein, the reference indicator is activated and/or marked by the UV laser leaving a permanent or semi-permanent reference readable by a machine and/or a human.

Substrate 12 is preferably substantially planar and is made of any solid material and/or combination of material. Substrate 12 has a first surface 12a that is electrically conductive. Surface 12a has an electrical resistance of 100 meg. ohms-per-square or less.

Figure 3B:
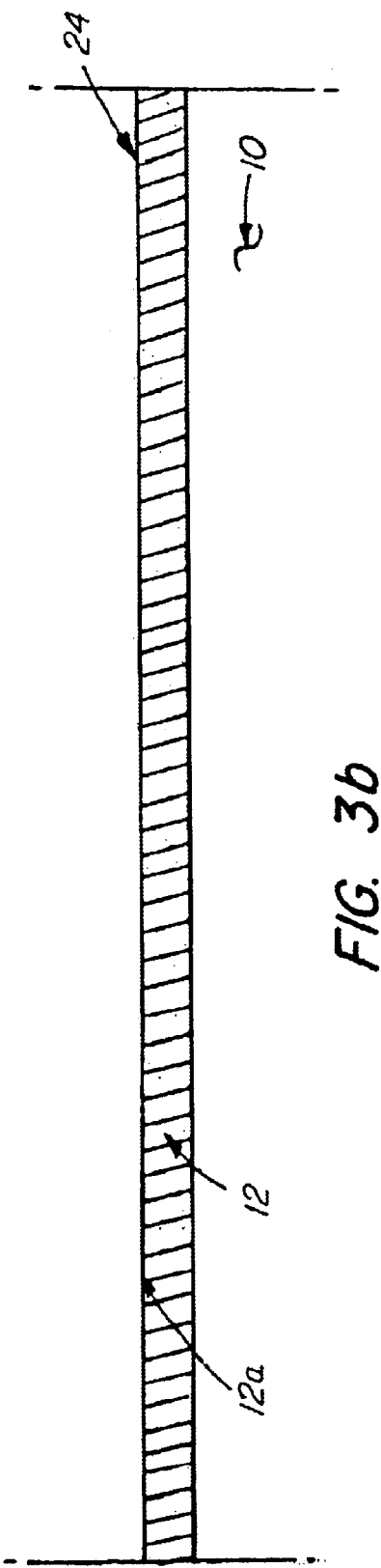
FIG. 3b is a cross-section at section B—B of FIG. 2b of a section of a channel sample plate in accordance with one embodiment of the invention.
Figure 4B:
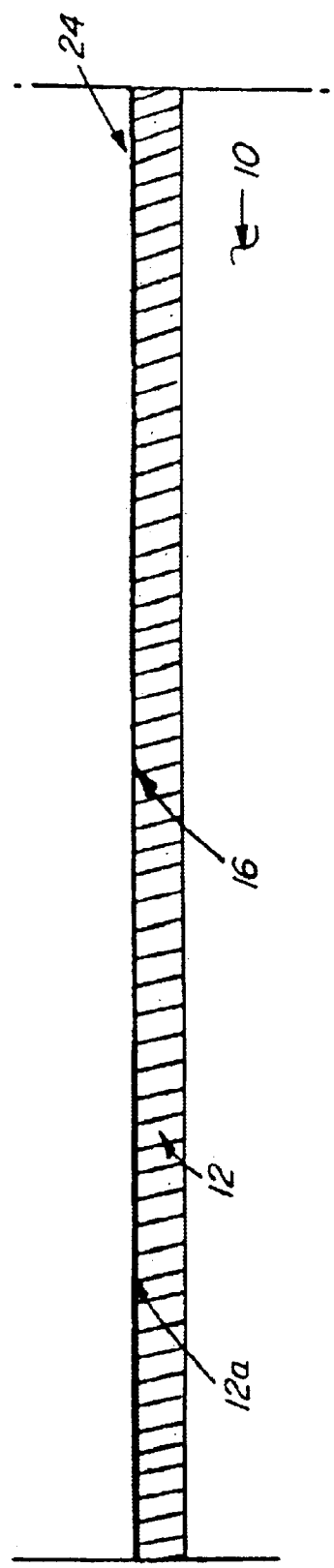
FIG. 4b is a cross-section at section B—B of FIG. 2b of a section of a channel sample plate with an electrically conductive coating applied to the substrate in accordance with one embodiment of the invention.

As illustrated in FIGS. 3a and 3b, substrate 12 may be made of electrically conductive materials; as for example using metals, metal alloys, electro-conductive plastics, and/or combinations thereof. In accordance with one embodiment of the invention, surface 12a is made electrically conductive using an electrically conductive coating 16 that is applied to substrate 12, as depicted in FIGS. 4a and 4b. Coating 16 may be any type of applied mass that has an electrical resistance of 100 meg. ohms-per-square or less. Preferably, coating 16 maintains the substantially planar shape of substrate 12. Coating 16 may be gold, copper, copper alloy, silver alloy, silver plating, conductive plastic, or a conductive polymer coating of any type. Preferably, the polymer coating includes Baytron P(3,4-polyethylenedioxythiophene-polystyrenesulfonate in water), CAS # 155090-83-8; polypyrrole, CAS # 30604-81, as a five percent (5%) water solution, or in a solvent-based solution; polyaniline as an emeraldine base, CAS # 5612-44-2; polyaniline as an emeraldine salt, CAS # 25233-30-1; and/or variants of polythiophenes, polyphenylenes, and/or polyvinylenes.

Mask 14 is selectively applied to surface 12a to form a mask that has a rough surface 14a wherein target area 24 is centrally located within sample site 20. Preferably, mask 14 has a thickness in the range of 1 to 100 $\mu$m and is made of a material that is relatively more hydrophobic than surface 12a and that maintains a suitable bond with substrate 12. For example, mask 14 may be made of polytetrafluoroethylene, commonly known as Teflon® and manufactured, sold, and/or licensed by DuPont Fluoroproducts of Wilmington, Del., or any other suitable material.

Rough surface 14a is a non-homogenous surface that is characterized by a coarse and/or an uneven surface quality and that is lacking uniform surface intensity, regardless whether surface 14a has a regular or repeating pattern or patterns of intensity, i.e. depth and/or graduations of the surface and/or material thickness.

In accordance with one embodiment of the invention, mask 14 may be adulterated, i.e. doped, with one or more marking agents that upon mass spectrometric analysis is/are detected as one or more markers as a predetermined analytical result or is detected by another means such as visual reference by an operator who sees the color effect of a marking agent. Such marking agents may be used for instrument calibration; quality assurance of sample preparation, handling, laboratory procedures, and/or sample tracking; quality assurance during production of sample plate 10; and/or handling. Examples of marking agents may be carbon black, titanium oxide, ferrous oxide, aluminum trioxides, polymeric materials, coloring materials, and/or others.

Figure 16:
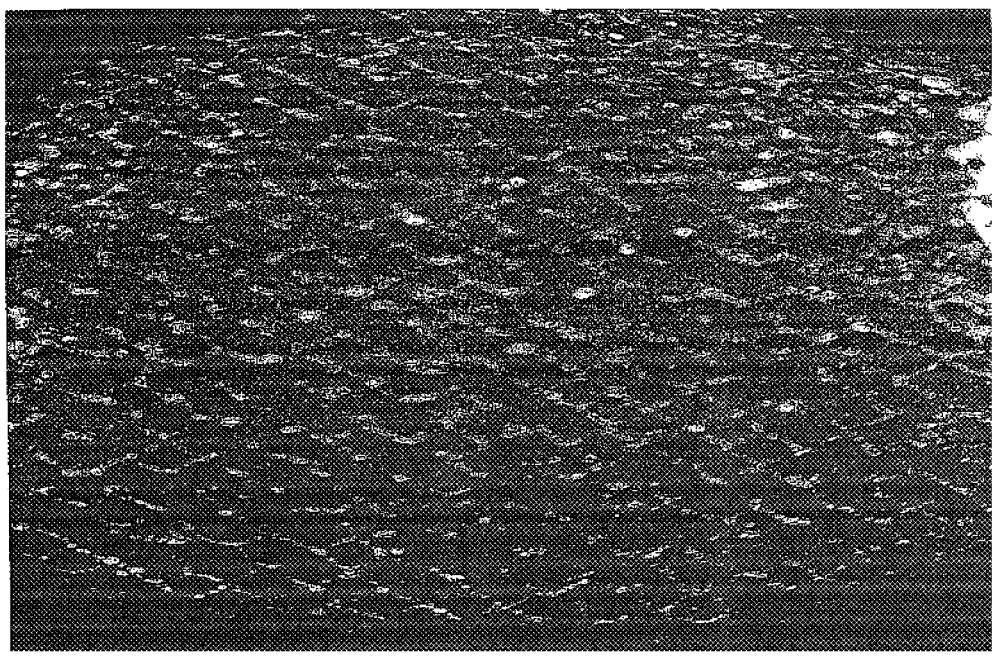
FIG. 16 is a photograph of a mask having a rough surface in accordance with one embodiment of the present invention.

In accordance with one embodiment of the invention, mask 14 is applied to surface 12*a* with a predetermined rough surface 14*a*. For example, mask 14 is applied using a screening application process resulting in rough surface 14*a*. Preferably, mask 14 is applied utilizing Teflon® with a screen mesh sizes ranging from 30×30 $\mu$m to 500×500 $\mu$m such resulting rough surface being described by the mesh size. Other screen sizes may be employed equally well. Upon screening, sample plate 10 is allowed to air dry, and once dry is heated to at least 50 Celsius to bond mask 14 with substrate 12. Referring to FIG. 16, a microscopic photograph of mask having rough surface is shown. The mask is made of black Teflon and is shown having a matted appearance. In this case, the matted appearance shows repeating substantially square shaped imperfections to the polymer surface substantially similar in size and shape as the mesh screen applied to the mask to form rough surface.

In accordance with one embodiment of the invention, physical and/or chemical manipulation of the material of mask 14 is used to texture and create a rough surface 14*a*. For example etching, gouging, scraping, oxidation, photo-oxidation, lithographic printing, off-set printing, reverse image accessing, and/or any other means may be used. In manufacturing the invention, rough surface may be applied to mask while mask is being applied to the substrate, or after it has been fixed to the surface.

Sample site 20 includes target area 24 and peripheral margin 22 of mask 14 that surrounds target area 24. Target area 24 is an area of electrically conductive surface 12*a* and may have a number of equally preferred embodiments, including embodiments wherein target area 24 includes a mask spot or other structure. In accordance with one embodiment of the invention, target area 24 has a circular plan area as depicted in FIG. 1*a* for a circle sample plate 10. In accordance with one embodiment of the invention, target area 24 has a rectangular, linear, and/or curvilinear plan area as depicted in FIG. 1*b* for a channel sample plate 10. Target area 24 may also be embodied having other plan areas.

As will be described further herein, target area 24 serves to substantially attract specimen 40 while it is in the liquid drop state. Specimen 40 is attracted to target area 24 because mask 14 is relatively more hydrophobic than target area 24.

In the circle sample plate 10 depicted in FIG. 1*a*, sample site 20 includes target area 24 having a circular plan area of surface 12*a* and peripheral margin 22 coincident with the maximum diameter in plan view with specimen 40 upon spotting on target area 24. Since the size of drops of specimen 40 may vary depending on investigative need, i.e. using a large drop to increase investigative sensitivity when biomolecules are in low concentration, target area 24 may be of different sizes to accommodate differently sized drops and sample plate 10 may be selected based upon a diameter of target area 24 that is sized appropriately for the drop size of specimen 40 that is to be investigated.

As is easily understood, the volume of a drop of a liquid directly correlates to the diameter of any planar section of the drop. As is further understood, plan and radial dimensions of a drop of liquid may be predetermined by controlling the drop's volume and determining the relative hydrophilic and/or hydrophobic qualities of the surface to which it adheres. Thus, control of drop size may be achieved using pipetting or any other method to control the volume of specimen 40.

It is known that hydrophobic and/or hydrophilic qualities are relative to the contact angle between a drop and the surface to which it adheres. An angle of 0° indicates total hydrophilic wetting of the surface and an angle of 180° indicates total hydrophobicity of the surface. Teflon® typically has a contact angle of 140° to 160° for water.

In channel sample plate 10 depicted in FIG. 1*b*, sample site 20 includes target area 24 having a plan area of surface 12*a*, characterized by length exceeding width, and a peripheral margin 22 substantially parallel to target area 24 coincident with the maximum diameter in plan view of specimen 40 or the maximum diameter in plan view of a plurality of specimen 40. Preferably, target area 24 has a width of 0.1 to 0.5 mm and sample plate 10 may be selected based upon a width of target area 24 that is sized appropriately for the volume of specimen 40 that is to be investigated.

In accordance with one embodiment of the invention, sample site 20 includes target area 24 having a rectangular plan area.

In accordance with one embodiment of the invention, sample site 20 includes target area 24 having a curvilinear plan area comprising a spiral, although other curvilinear plan areas such as a series of concentric plan areas are also contemplated.

Figure 2C:
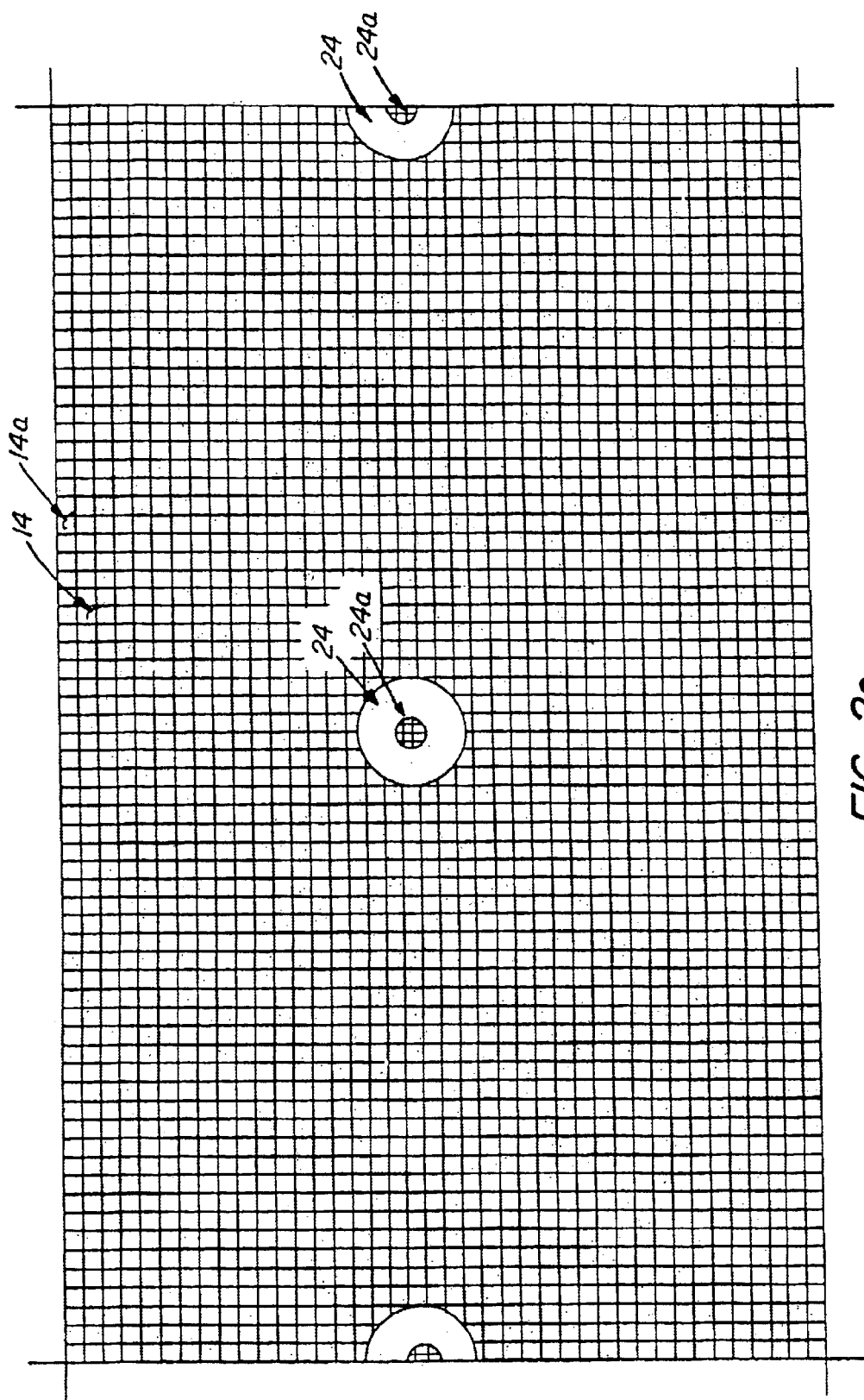
FIG. 2c is a plan view of a circle sample site that includes a target area and a mask spot in accordance with one embodiment of the invention.

In accordance with one embodiment of the invention, mask 14 is additionally applied to a central region of target area 24 to form at least one mask spot 24*a*. FIG. 2*c* is a plan view of a sample site that includes a target area and a mask spot in accordance with one embodiment of the invention. FIG. 3*c* is an expanded elevation view of a sample site that includes a target area and a mask spot in accordance with one embodiment of the invention. Mask spot 24*a* is further explained herein.

FIG. 5 through FIG. 10 depict the crystallization and crystals produced by the dried droplet method using specimen 40 on sample plate 10 in accordance with one embodiment of the invention. FIG. 5*a* is an enlarged view taken at area A—A of FIG. 1*a* of a circle sample plate in accordance with one embodiment of the invention wherein specimens have been applied on sample sites. FIG. 5*b* is an enlarged view taken at area A—A of FIG. 1*b* of a channel sample plate in accordance with one embodiment of the invention wherein specimens have been applied on sample sites.

Figure 5A:
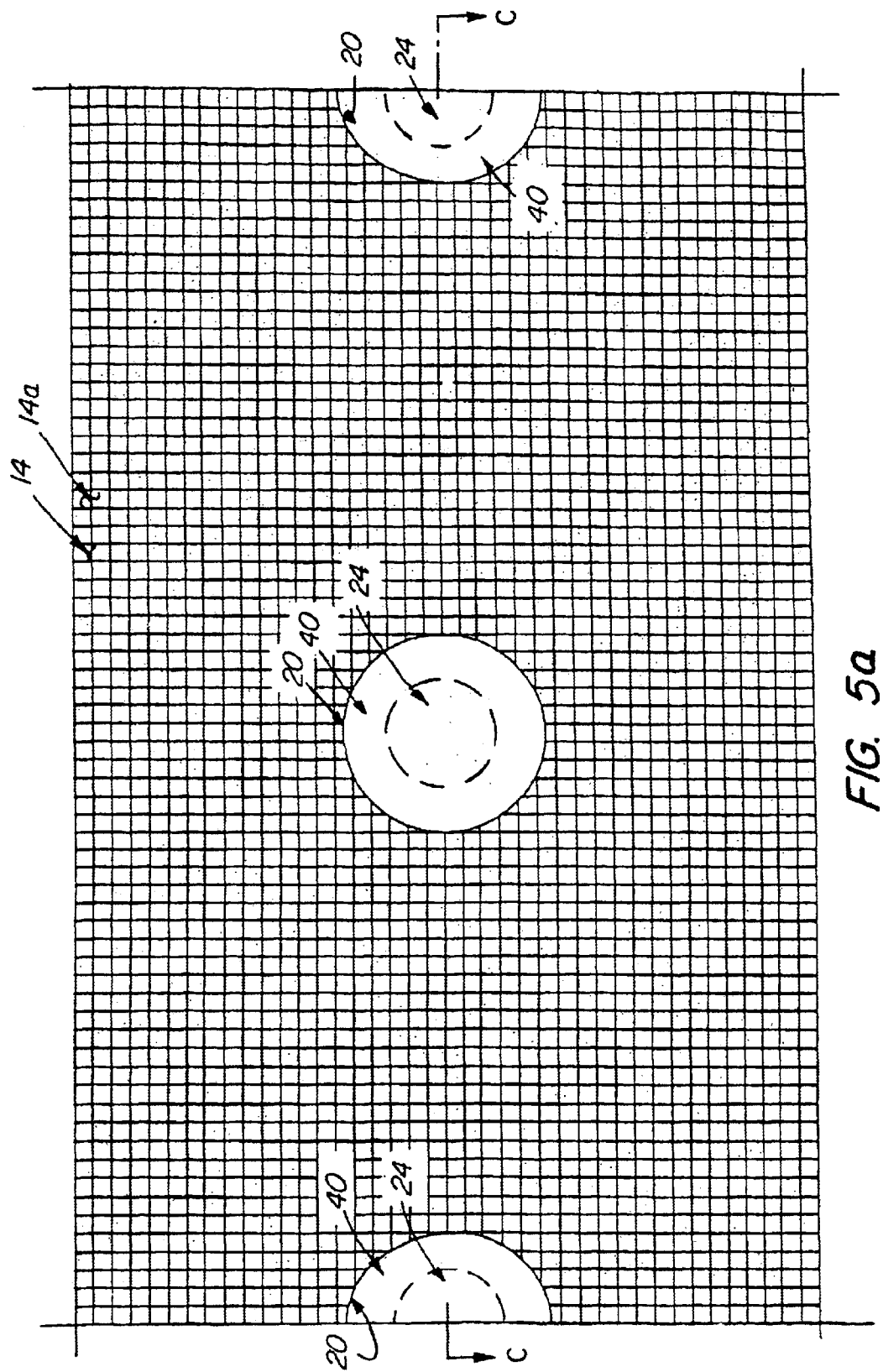
FIG. 5a is an enlarged view taken at area A—A of FIG. 1a of a circle sample plate in accordance with one embodiment of the invention wherein specimens have been applied on sample sites.
Figure 5B:
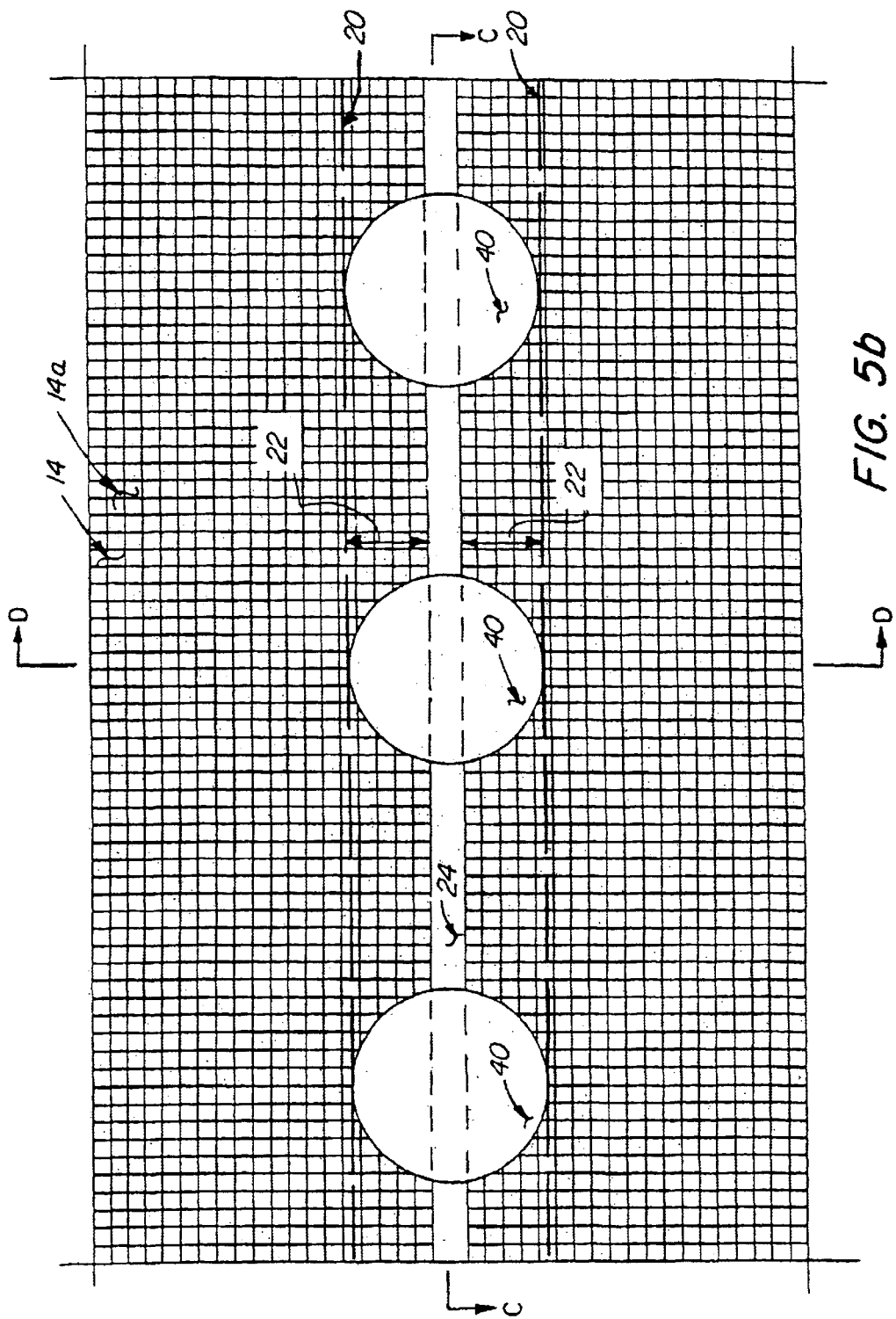
FIG. 5b is an enlarged view taken at area A—A of FIG. 1b of a channel sample plate in accordance with one embodiment of the invention wherein specimens have been applied on sample sites.
Figure 6B:
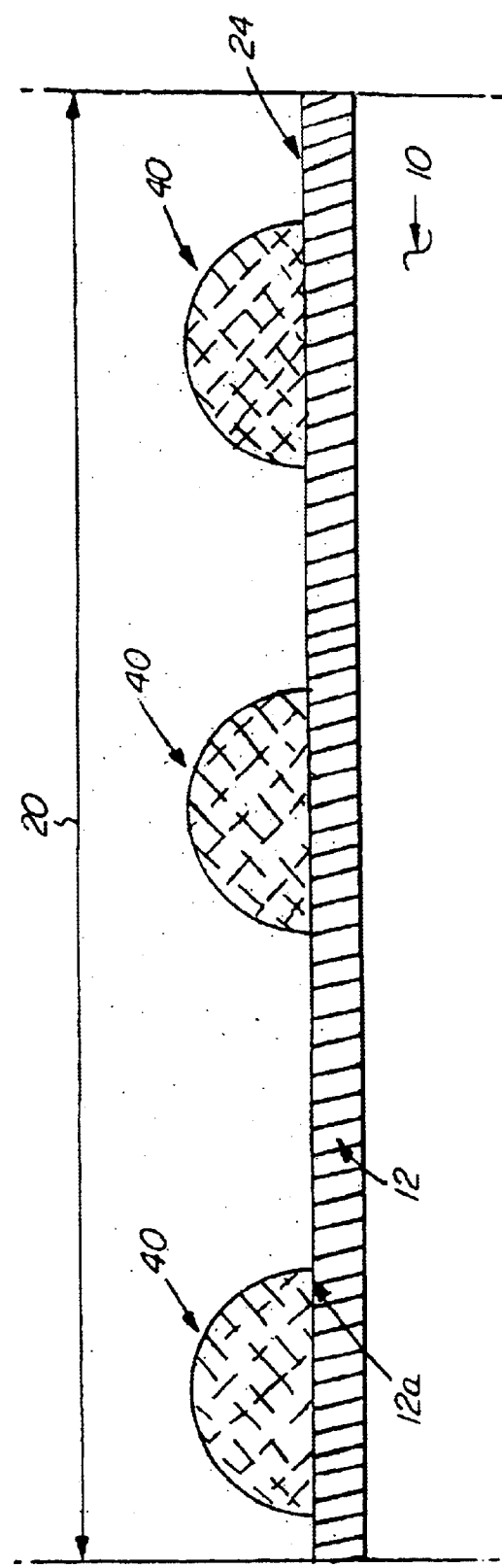
FIG. 6b is a cross-section at section C—C of FIG. 5b of a section of a channel sample plate in accordance with one embodiment of the invention wherein specimens have been applied on sample sites.

FIG. 6*a* is a cross-section at section C—C of FIG. 5*a* of a section of a circle sample plate in accordance with one embodiment of the invention wherein specimens have been applied on sample sites. FIG. 6*b* is a cross-section at section C—C of FIG. 5*b* of a section of a channel sample plate in accordance with one embodiment of the invention wherein specimens have been applied on sample sites. FIG. 6*b* is a cross-section at section D—D of FIG. 5*b* of a section of a channel sample plate in accordance with one embodiment of the invention wherein specimens have been applied on sample sites.

Figure 7A:
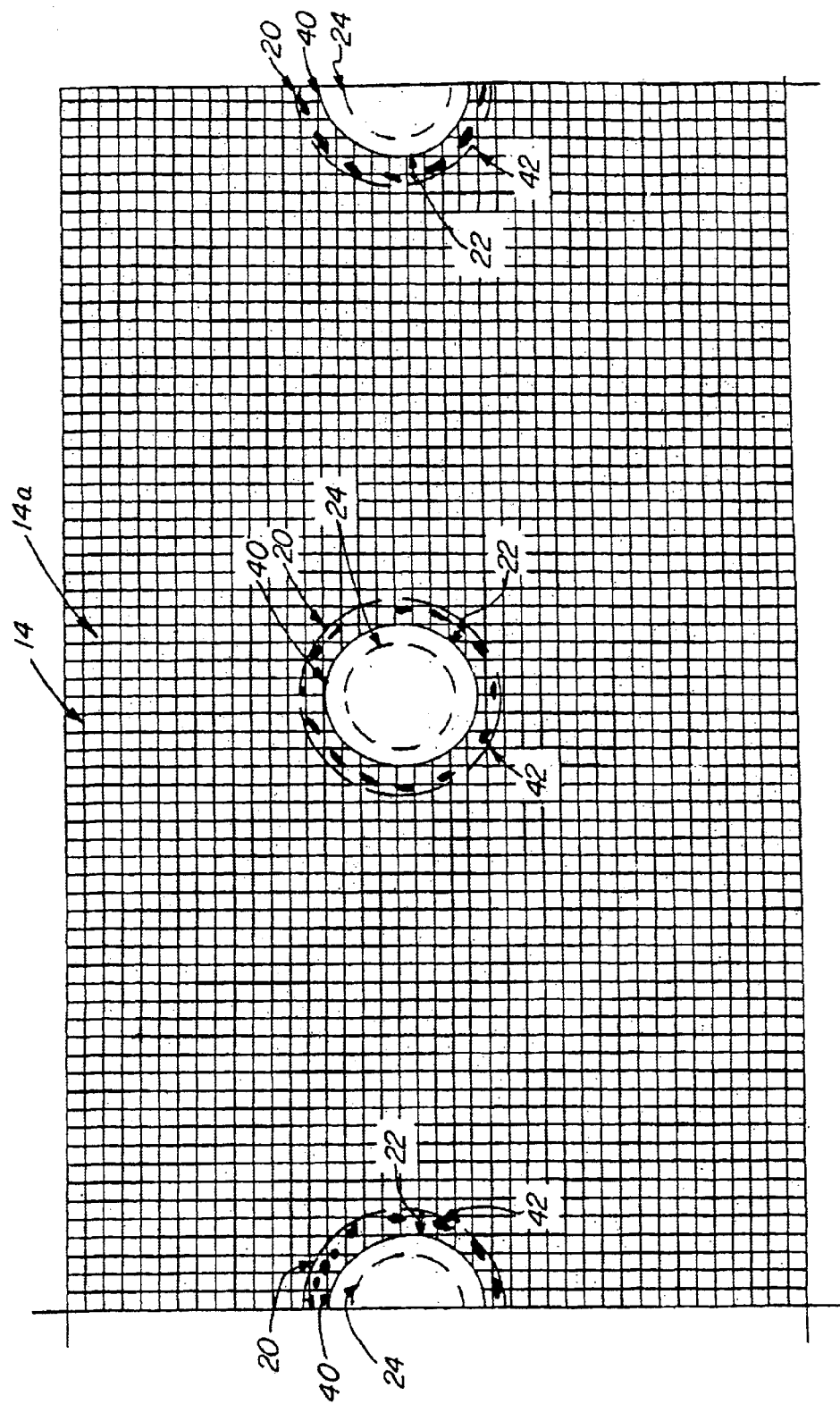
FIG. 7a is an enlarged view taken at area A—A of FIG. 1a of a circle sample plate in accordance with one embodiment of the invention wherein specimens of FIG. 6a have begun to dry.
Figure 7B:
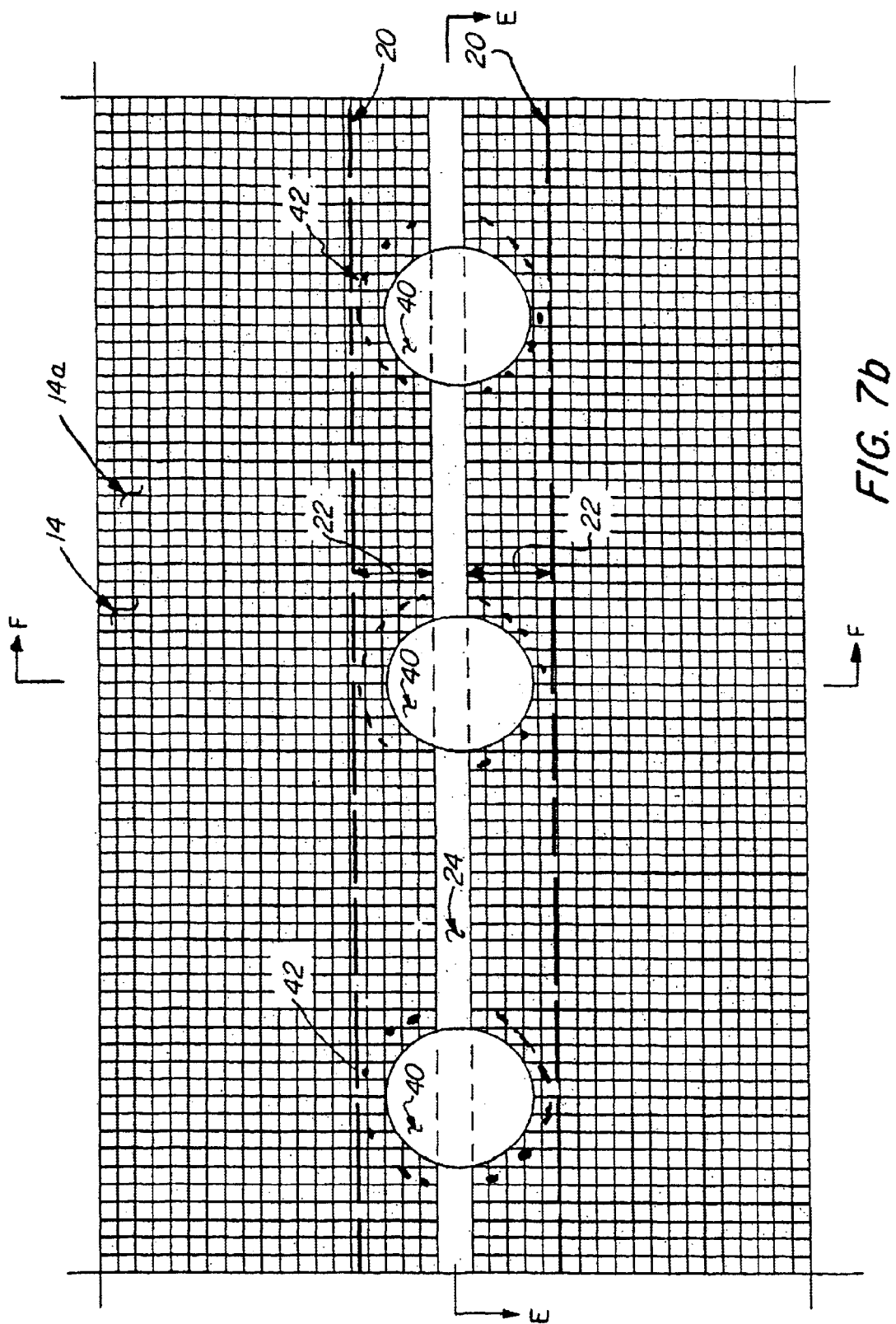
FIG. 7b is an enlarged view taken at area A—A of FIG. 1b of a channel sample plate in accordance with one embodiment of the invention wherein specimens of FIG. 6b have begun to dry.

FIG. 7*a* is an enlarged view taken at area A—A of FIG. 1*a* of a circle sample plate in accordance with one embodiment of the invention wherein specimens of FIG. 6*a* have begun to dry. FIG. 7*b* is an enlarged view taken at area A—A of FIG. 1*b* of a channel sample plate in accordance with one embodiment of the invention wherein specimens of FIG. 6*b* have begun to dry.

Figure 8B:
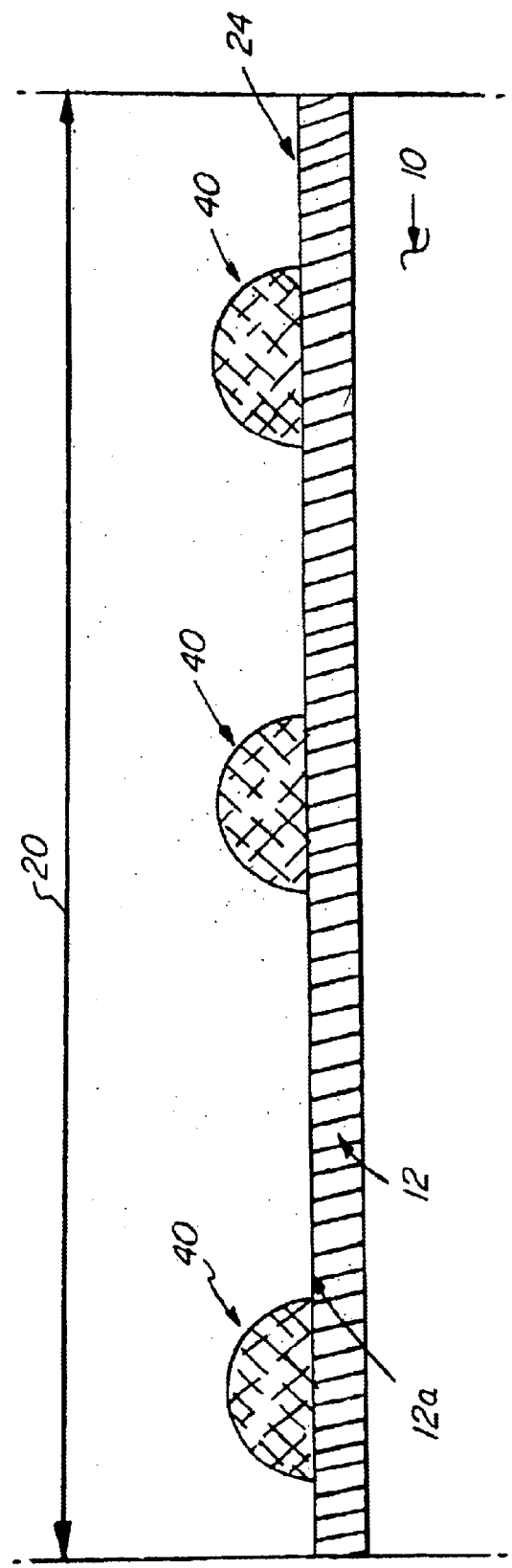
FIG. 8b is a cross-section at section E—E of FIG. 7b of a section of a channel sample plate in accordance with one embodiment of the invention wherein specimens of FIG. 6b have begun to dry.

FIG. 8a is a cross-section at section E—E of FIG. 7a of a section of a circle sample plate in accordance with one embodiment of the invention wherein specimens of FIG. 6a have begun to dry. FIG. 8b is a cross-section at section E—E of FIG. 7b of a section of a channel sample plate in accordance with one embodiment of the invention wherein specimens of FIG. 6b have begun to dry. FIG. 8c is a cross-section at section F—F of FIG. 7b of a section of a channel sample plate in accordance with one embodiment of the invention wherein specimens of FIG. 6b have begun to dry.

Figure 9A:
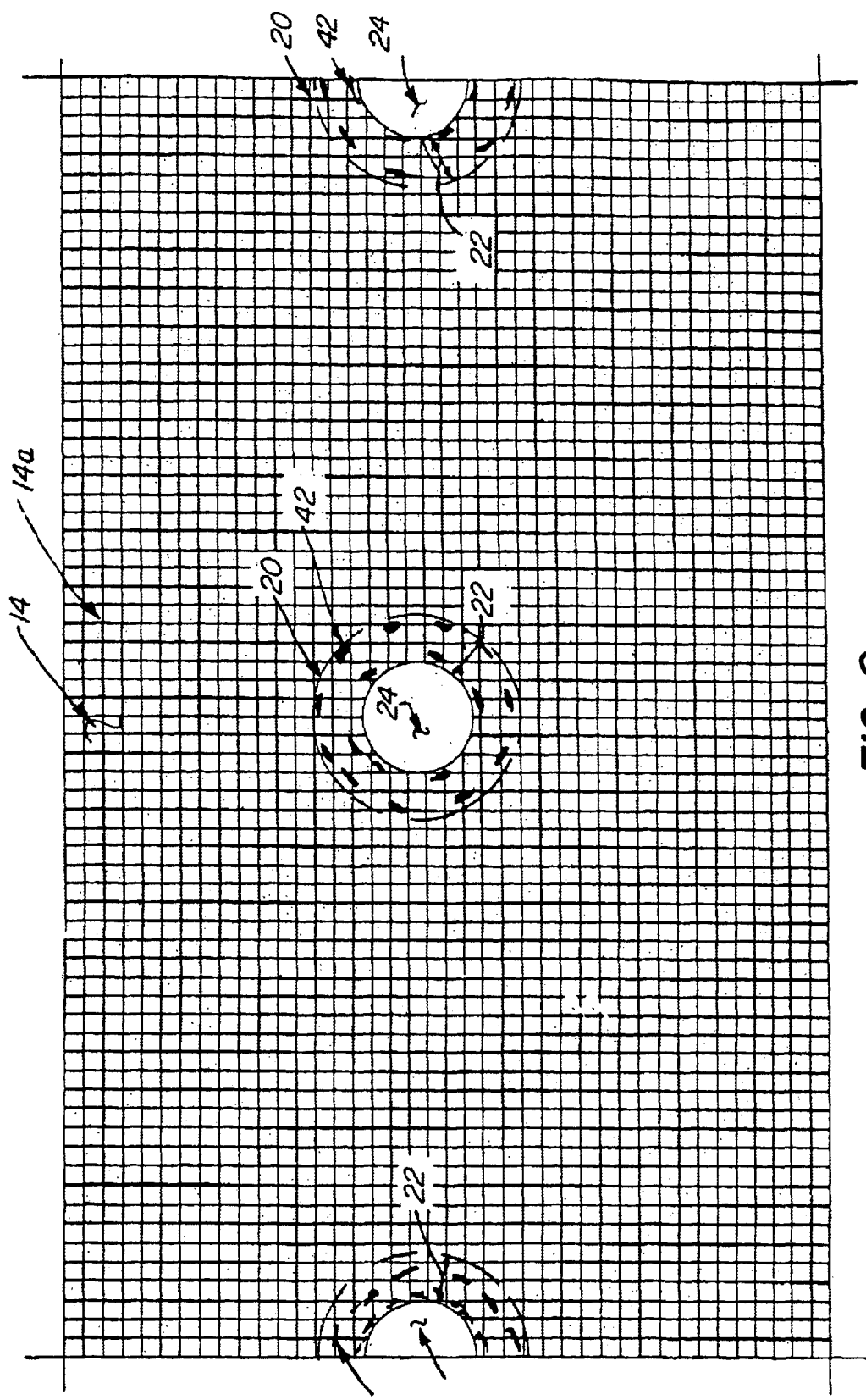
FIG. 9a is an enlarged view taken at area A—A of FIG. 1a of a circle sample plate in accordance with one embodiment of the invention wherein specimens of FIG. 6a have dried.
Figure 9B:
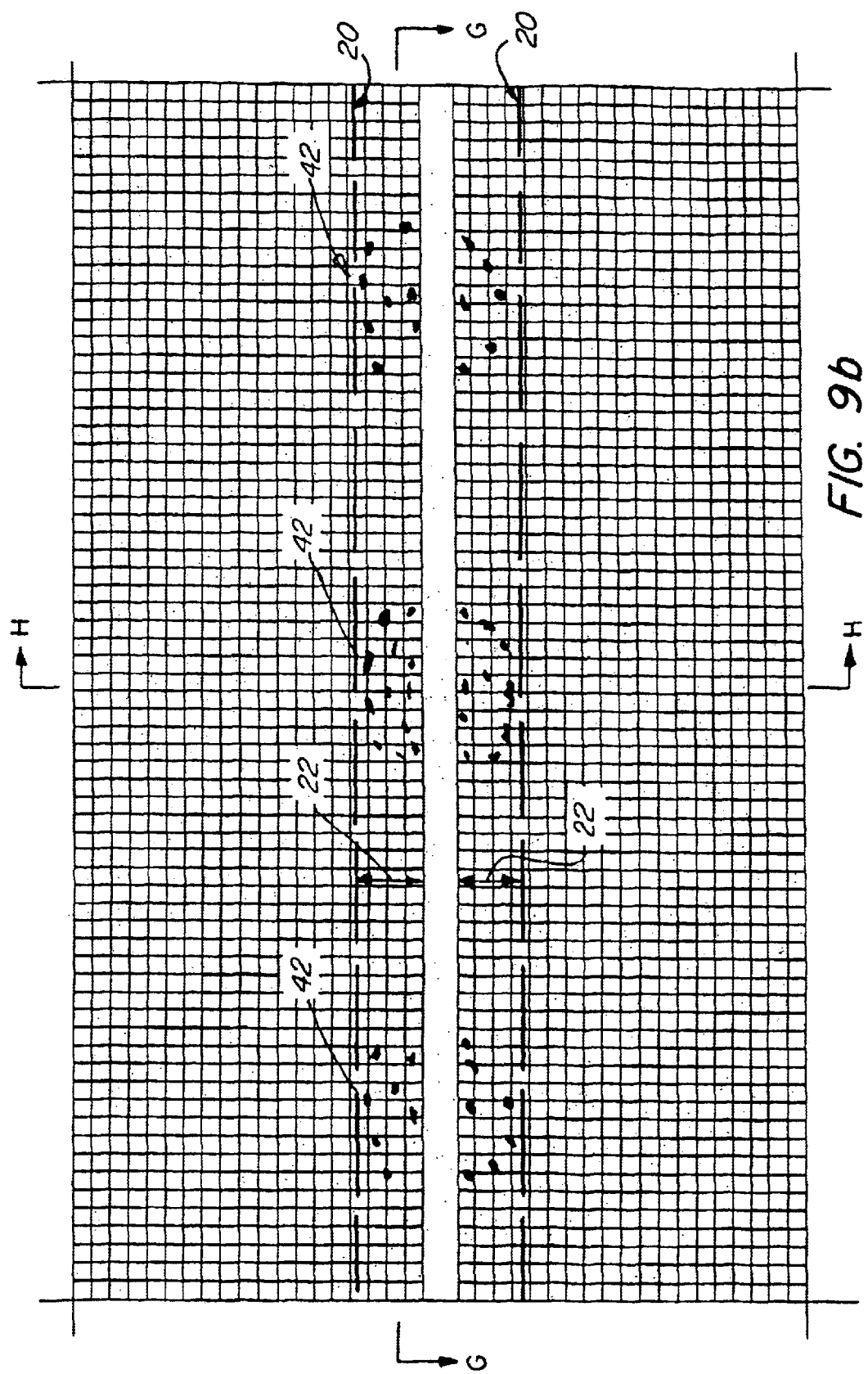
FIG. 9b is an enlarged view taken at area A—A of FIG. 1b of a channel sample plate in accordance with one embodiment of the invention wherein specimens of FIG. 6b have dried.

FIG. 9a is an enlarged view taken at area A—A of FIG. 1a of a circle sample plate in accordance with one embodiment of the invention wherein specimens of FIG. 6a have dried. FIG. 9b is an enlarged view taken at area A—A of FIG. 1b of a channel sample plate in accordance with one embodiment of the invention wherein specimens of FIG. 6b have dried.

Figure 10A:
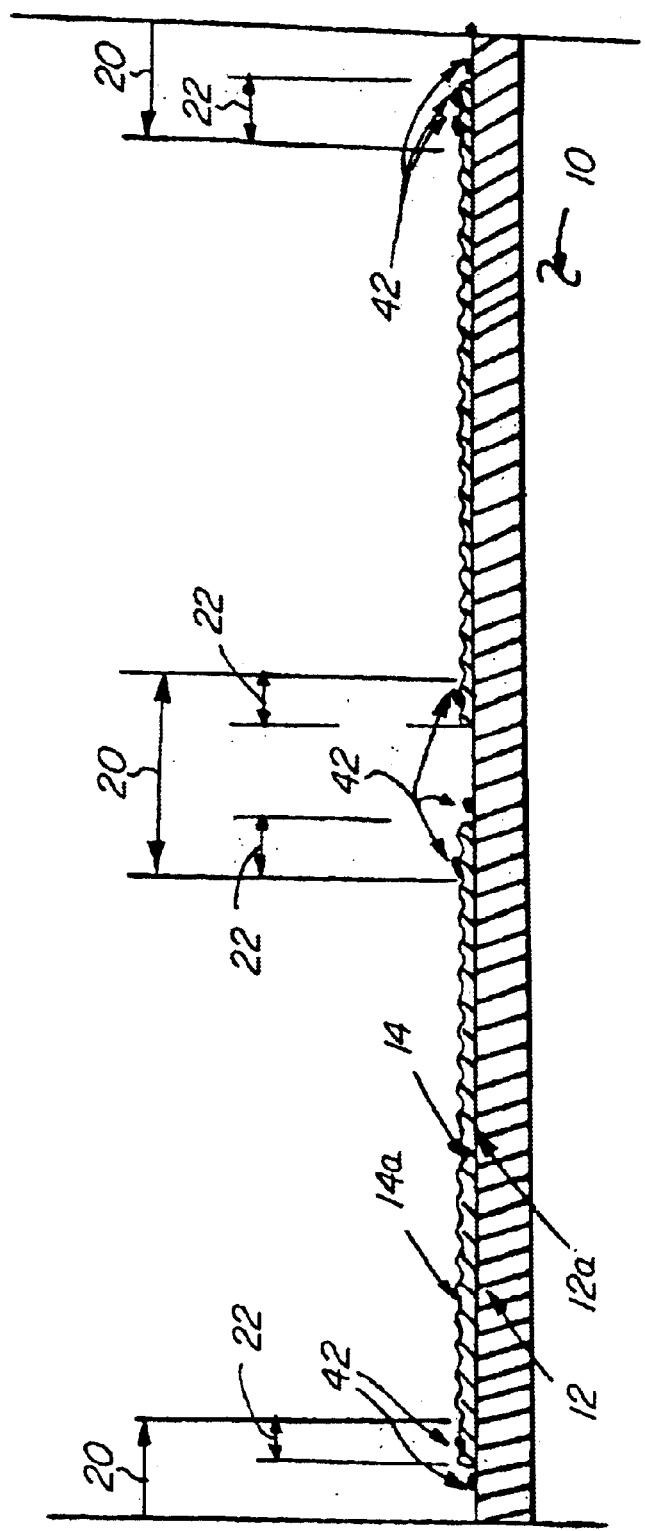
FIG. 10a is a cross-section at section G—G of FIG. 9a of a section of a circle sample plate in accordance with one embodiment of the invention wherein specimens of FIG. 6a have dried.
Figure 10C:
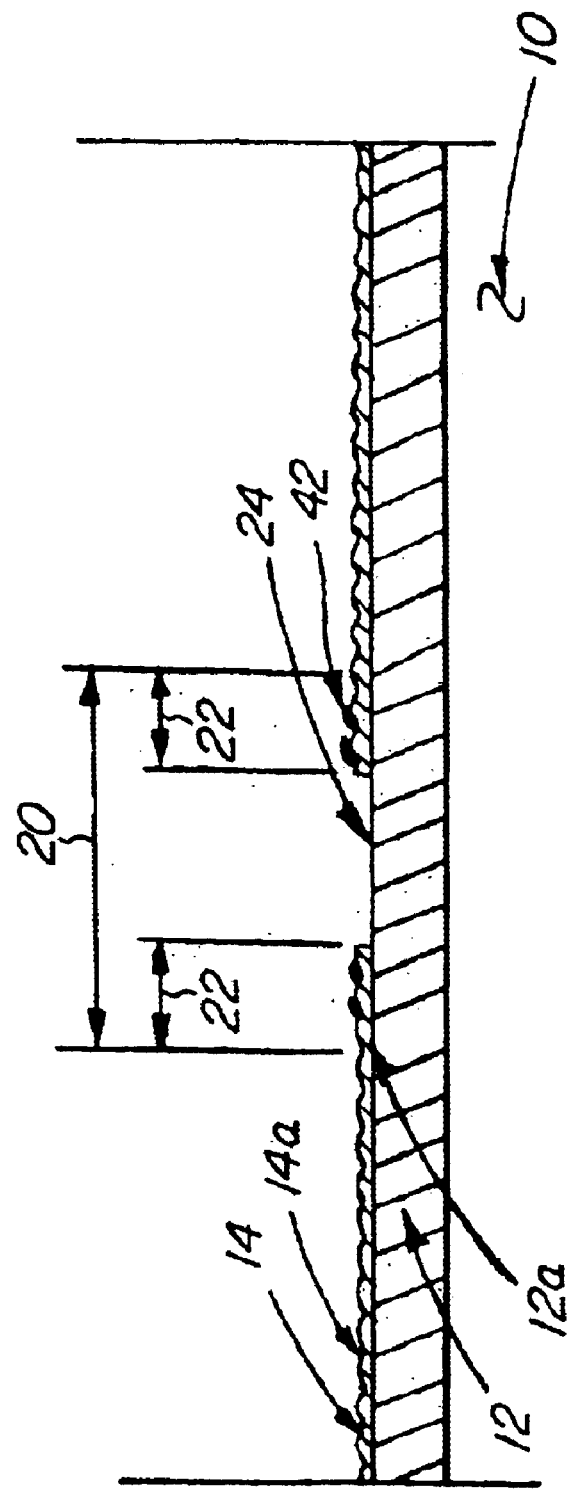
FIG. 10c is a cross-section at section H—H of FIG. 9b of a section of a circle sample plate in accordance with one embodiment of the invention wherein specimens of FIG. 6b have dried.

FIG. 10a is a cross-section at section G—G of FIG. 9a of a section of a circle sample plate in accordance with one embodiment of the invention wherein specimens of FIG. 6a have dried. FIG. 10b is a cross-section at section G—G of FIG. 9b of a section of a channel sample plate in accordance with one embodiment of the invention wherein specimens of FIG. 6b have dried. FIG. 10c is a cross-section at section H—H of FIG. 9b of a section of a circle sample plate in accordance with one embodiment of the invention wherein specimens of FIG. 6b have dried.

Specimens 40, each consisting of a drop in liquid form, are applied to sample plate 10 within sample site 20 and contact mask 14. Therein, it is preferred that specimen 40 contact mask 14 at the sides over a distance of at least 0.1 mm.

For circle sample plate 10, specimen 40 contacts mask 14 in plan view at the perimeter of target area 24 by using a drop of specimen 40 where the drop's maximum diameter exceeds the diameter of target area 24. Since, it is known that a drop with a volume of 0.5 $\mu$l has diameter of approximately 1.0 mm on the hydrophobic surface of Teflon®, it is preferred that each specimen 40 is between 0.1 to 4.0 $\mu$l in volume.

For channel sample plate 10, specimen 40 contacts mask 14 in plan view at peripheral margin 22 while the perimeter of specimen 40 also contacts target area 24. In accordance with one embodiment of the invention, specimen 40 is applied within sample site 20 on channel sample plate 10 in a continuous manner, such as by spraying or streaking specimen 40. Therein, the width or length of the application of specimen 40 exceeds the width or length of target area 24, respectively, so that specimen 40 contacts mask 14.

In accordance with one embodiment of the invention, mask spot 24a is appropriately sized to form a drop of specimen 40 so that the drop contacts the side of mask 14 to enhance the deposition of crystals.

Specimen 40 includes a biomolecule and a matrix mixed in a 1:1 ratio, by volume. Although other formulations including those with low solubility may also advantageously be used and the formulations presented herein are not intended to be limiting, the matrix may be made according to the following formulations:

In a first formulation (CHCA formulation), α-cyano-4-hydroxycinnamic acid ($C_{10}H_7NO_3$) and an aqueous solution containing a solvent are mixed to produce a matrix. The solvent preferably is acetonitrile ($C_2H_3N$) and is mixed at a ratio of 30% to 50% acetonitrile and 50% to 70% water, respectively, with 0.1% trifluoroacetic acid ($C_2HF_3O_2$), pH 2.3, by volume, to produce a solvent. CHCA may be present at a concentration of 0.2 mg to 20 mg per 1 ml of solvent, although a concentration of 1 to 5 mg of CHCA per 1 ml of solvent is preferred. The first formulation may utilize other matrices such as other cinnaminic acids or other matrices of low solubility instead of CHCA.

In a second formulation (SA formulation), 3,5-dimethoxy-4-hydroxycinnamic acid ($C_{11}H_{12}O_5$), commonly known as sinapinic acid, and an aqueous solution containing a solvent are mixed to produce a matrix. The solvent preferably is acetonitrile ($C_2H_3N$) and is mixed at a ratio of 30% to 50% acetonitrile and 70% to 50% water with 0.1% trifluoroacetic acid ($C_2HF_3O_2$), pH 2.3, by volume, to produce a solvent. Sinapinic acid may be present at a concentration of 0.2 mg to 20 mg per 1 ml of solvent, although a concentration of 1 to 5 mg of sinapinic acid per 1 ml of solvent is preferred.

The CHCA formulation is preferred for analysis of biomolecules such as peptides and other biomolecules having molecular weights of less than 10,000 Daltons. The SA formulation is preferred for biomolecules such as proteins and other biomolecules having molecular weights of 10,000 Daltons and more.

Figure 11:
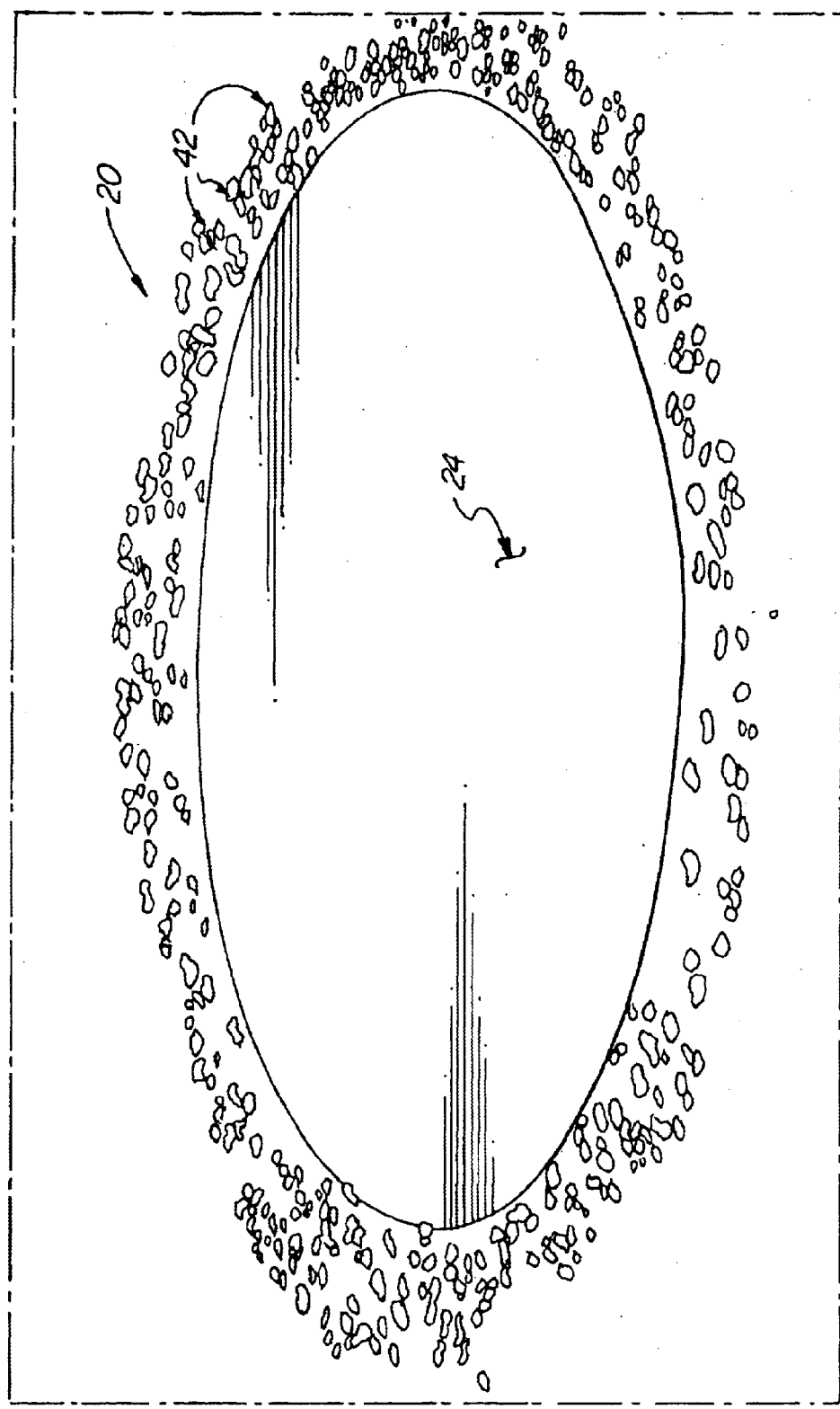
FIGS. 11 and 12 are isometric views of crystals that have crystallized in a halo effect around a sample site with different concentrations of matrix formulations in accordance with one embodiment of the invention.
Figure 12:
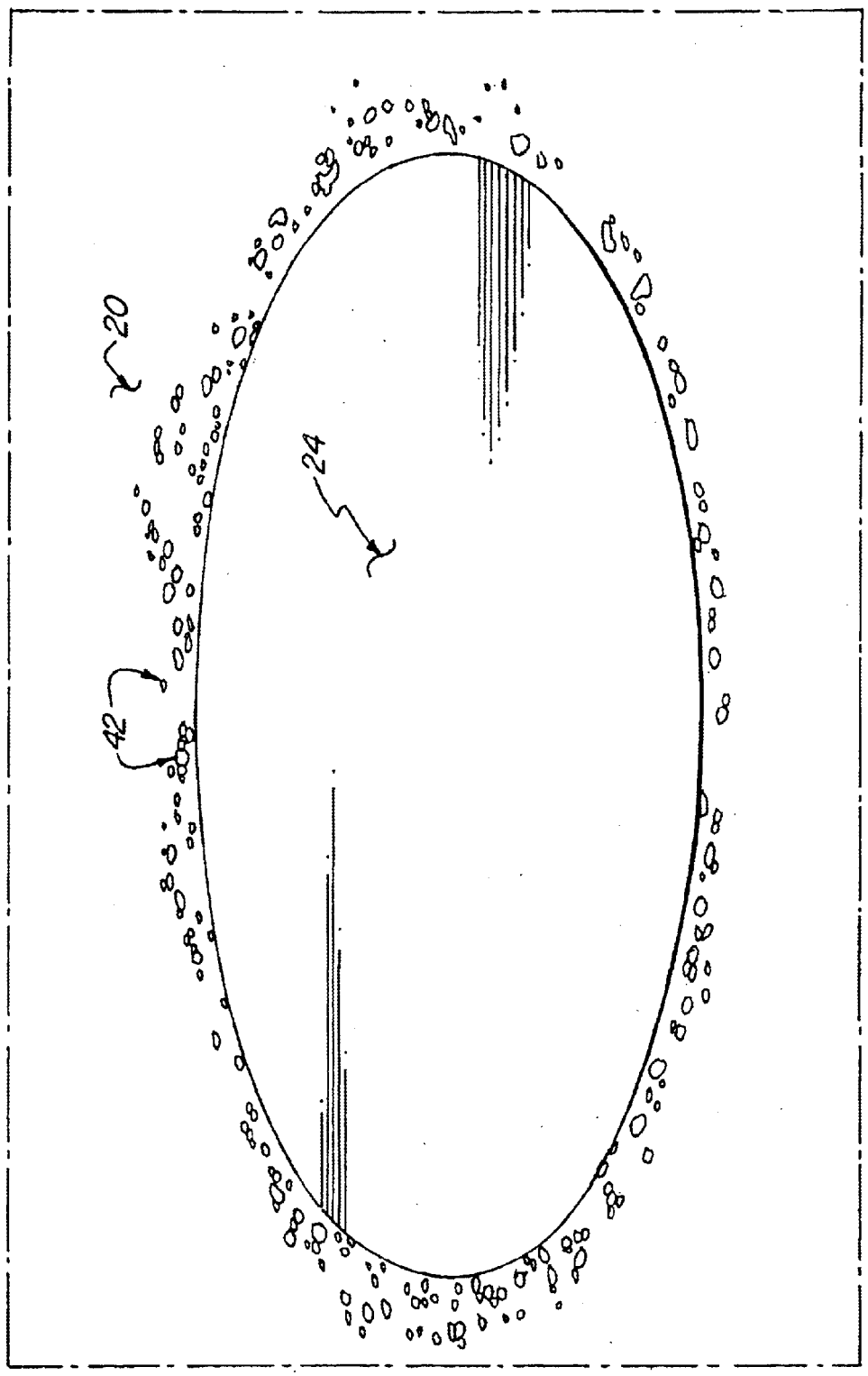

FIGS. 11 and 12 are isometric views of crystals that have formed in a halo effect in a sample site with different concentrations of matrix formulations in accordance with one embodiment of the invention. For simplicity, a sample site 20 of circle sample plate 10 is depicted. Therein, crystals 42 deposit on rough surface 14a in margin 22, forming a halo effect around the perimeter of target area 24. Further crystals 42 form as the sample solution dries and crystals 42 continue to form on surface 14a on margin 22 on sample site 20. While crystals 42 are greatest in number in margin 22, a significantly smaller amount deposit on target area 24.

Figure 17:
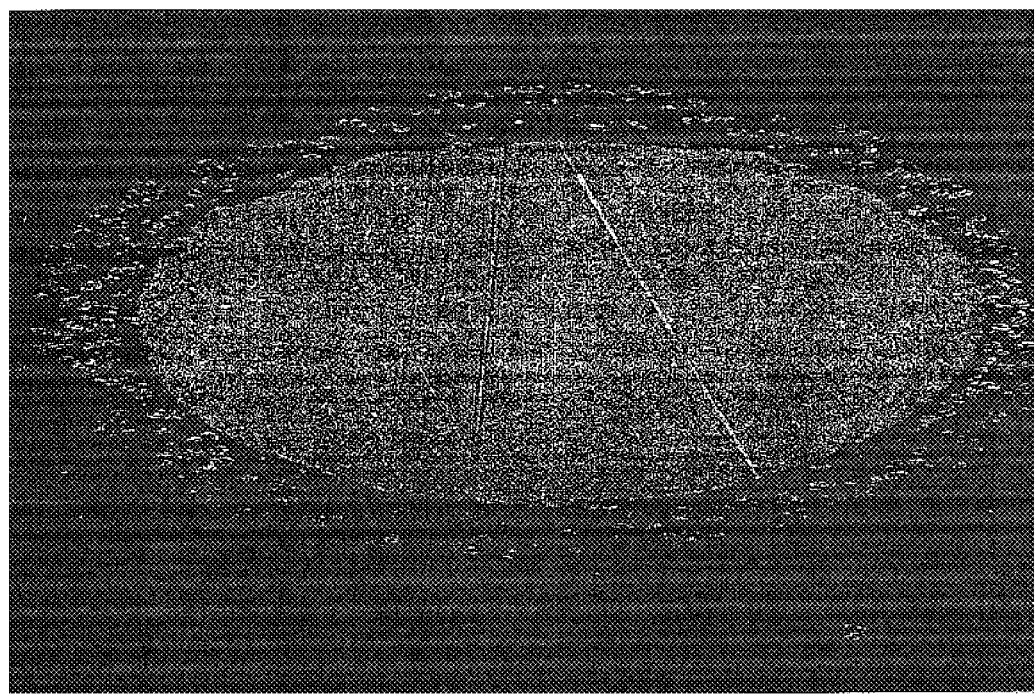
FIG. 17 is a photograph showing crystals that have crystallized around a sample site in accordance with one embodiment of the invention.

FIG. 11 depicts crystals 42 on sample site 20 of circle sample plate 10 produced using CHCA matrix solution at a concentration of 1 mg of CHCA per 1 ml of solvent. Crystals 42 crowd margin 22 near the periphery of target area 24 approximately forming two concentric crystal rings around the periphery. A third ring is approximately present in some areas. FIG. 17 is a photograph of a similar sample showing crystals on sample site of circle sample plate produced using CHCA matrix solution at a concentration of 1 mg of CHCA per 1 ml of solvent. Crystals crowd margin near the periphery of target area forming crystal rings around the periphery.

Figure 18:
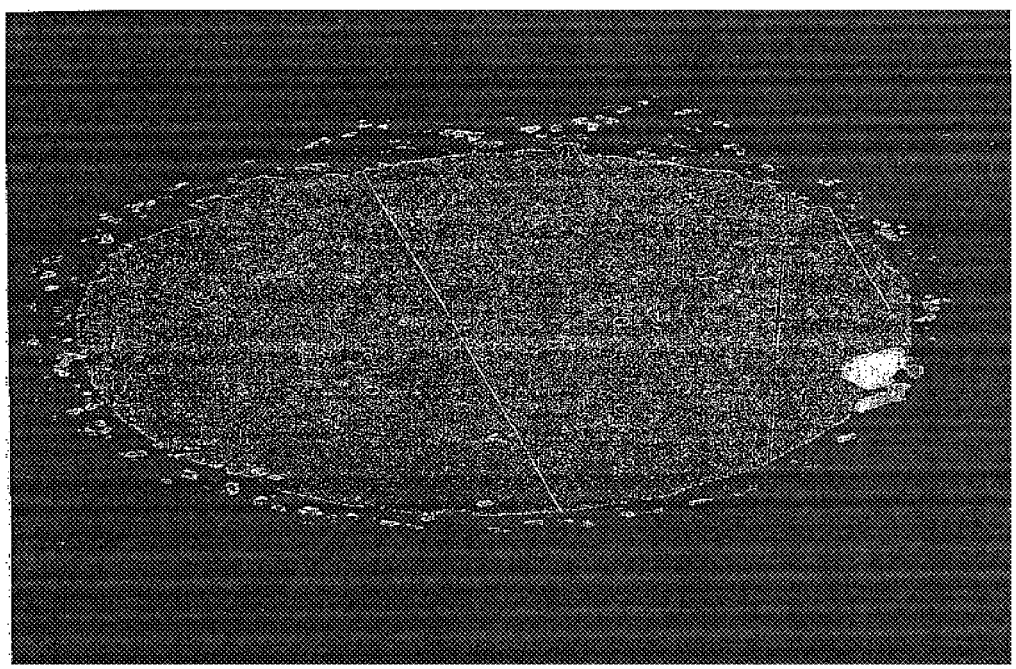
FIG. 18 is a photograph showing crystals that have crystallized around a sample site in accordance with one embodiment of the invention using a specimen different than that shown in FIG. 17.

Crystal rings are believed to result from the increase in matrix concentration during the concomitant decrease in solvent volume as the solvent evaporates. Crystalline lattices begin to form and are attracted to rough surface 14a known to induce crystalline formation. As the specimen drop dries, many matrix crystalline lattices precipitate from the solution at roughly the same time. Such precipitation occurs at regular intervals leading to deposition in ring. As the larger matrix crystals precipitate, smaller crystals form anew while the specimen drop continues drying. Eventually these smaller crystals 42 also are unsustainable in solution and precipitate from solution. In contrast, where a lower concentration of matrix is used, crystals 42 result in only one ring. Such crystals 42 are depicted in FIG. 12 where crystal 42 on sample site 20 were produced using CHCA matrix solution at a concentration of 0.5 mg of CHCA per 1 ml of solvent. FIG. 18 is a photograph of sample showing crystals on sample site of circle sample plate produced using 30% ACN matrix solution at a concentration of 1 mg of per 1 ml of solvent. Crystals crowd margin near the periphery of target area forming crystal ring around the periphery.

To analyze the biomolecule, crystals 42 are irradiated using a UV laser (not shown for clarity) that scans crystals 42 directly using the energy of a laser beam. The UV laser generates a laser beam 48 typically at 337 nm wavelength, which may be any suitable ultra-violet laser beam such one having an effective beam diameter of 0.1 to 0.2 mm. As is easily understood, concentrating crystals 42 in margin 22 reduces the area required to be scanned by the laser in order to irradiate sufficient crystals 42 to obtain significant irradiation without compromising analysis sensitivity. Given the beam's relatively small effective diameter, reducing the requisite scanning area significantly enhances efficiency.

The reduced area is advantageously illustrated in comparison to the area that must be irradiated when a traditional formulation is used to produce specimen 40. To illustrate this example, 2,5-dihydroxybenzoic acid ($C_7H_6O_4$) known as DHB is used and is compared to the formulations of the present invention. In DHB formulations, crystals 42 occur in target area 24. Thus, in order to irradiate crystals 42 of the DHB formulation, the entire target area 24 must be scanned. Thus, if target area 24 has a diameter of 1 mm, the area to be scanned is $0.25\pi$ mm². In order to irradiate crystals 42 wherein the matrix is the CHCA or SA formulation and the sample site 20 has a diameter of 1.2 mm, the area to be scanned is the $0.11\pi$ mm². This results in a required scanning area that is only 44% of the traditional scanning area. FIG. 19 is a photograph of DHB crystals forming in the traditional target area, covering a large surface area.

Figure 13:
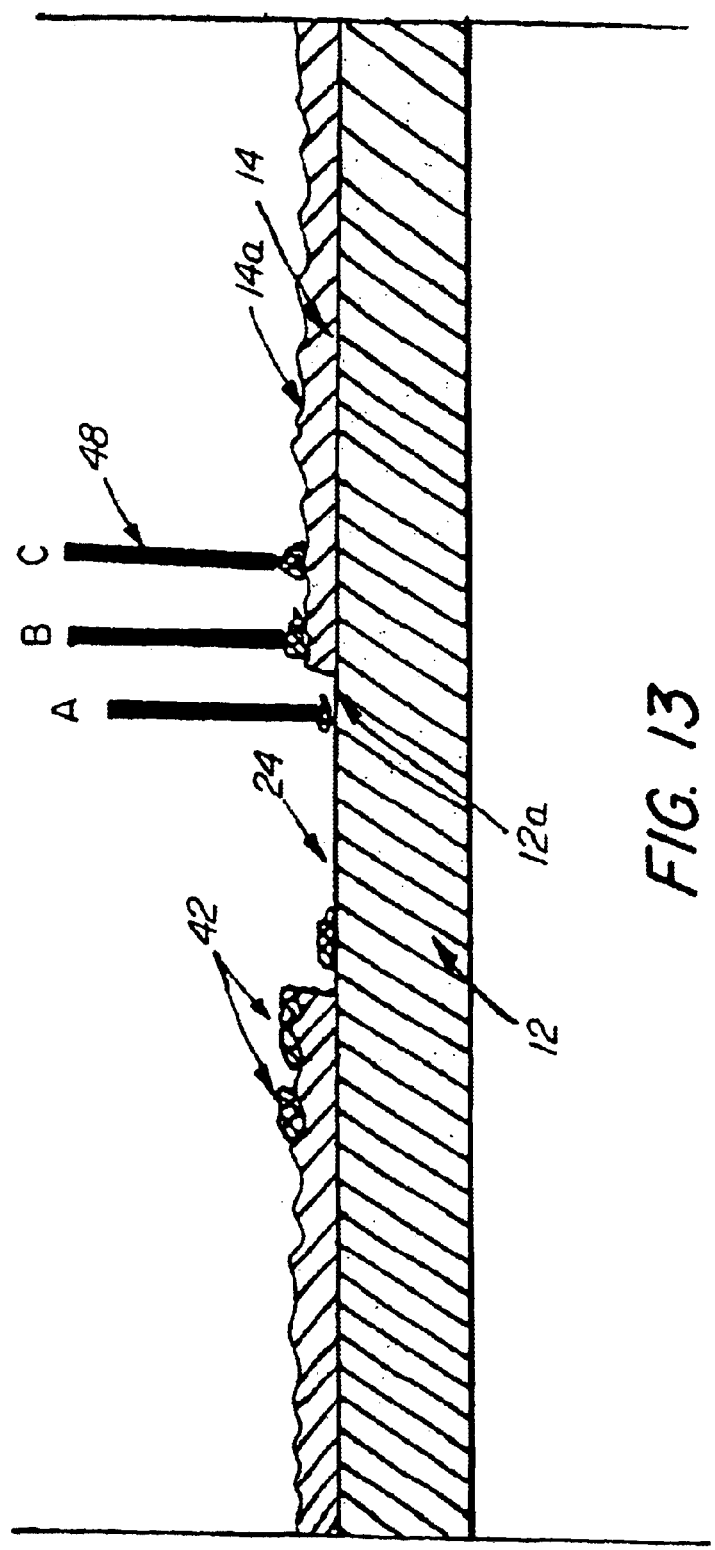
FIG. 13 is a cross-sections at section E—E of FIG. 5a of a section of a sample plate in accordance with one embodiment of the invention wherein crystals are being scanned by an UV laser.

FIG. 13 is a cross-section at section E—E of FIG. 5a of a section of a sample plate in accordance with one embodiment of the invention wherein crystals are being scanned by an UV laser. FIG. 13 illustrates the scanning of crystals 42 that were produced using the CHCA and SA formulation.

Laser beam 48 sweeps scanning pattern 50 (not shown for clarity) wherein it irradiates crystals 42 at a first position, marked by the letter A in FIG. 13. As pattern 50 continues, at a second position, marked by the letter B in FIG. 13, laser beam 48 irradiates another crystal 42 and proceeds further, where at a third position, marked by the letter C in FIG. 13, it irradiates another crystal 42, and so forth. Therein, it is understood that scanning pattern 50 may be accomplished by maintaining the laser stationary and moving plate 10, or by moving the laser and maintaining plate 10 stationary, and/or a combination of both.

Figure 14A:
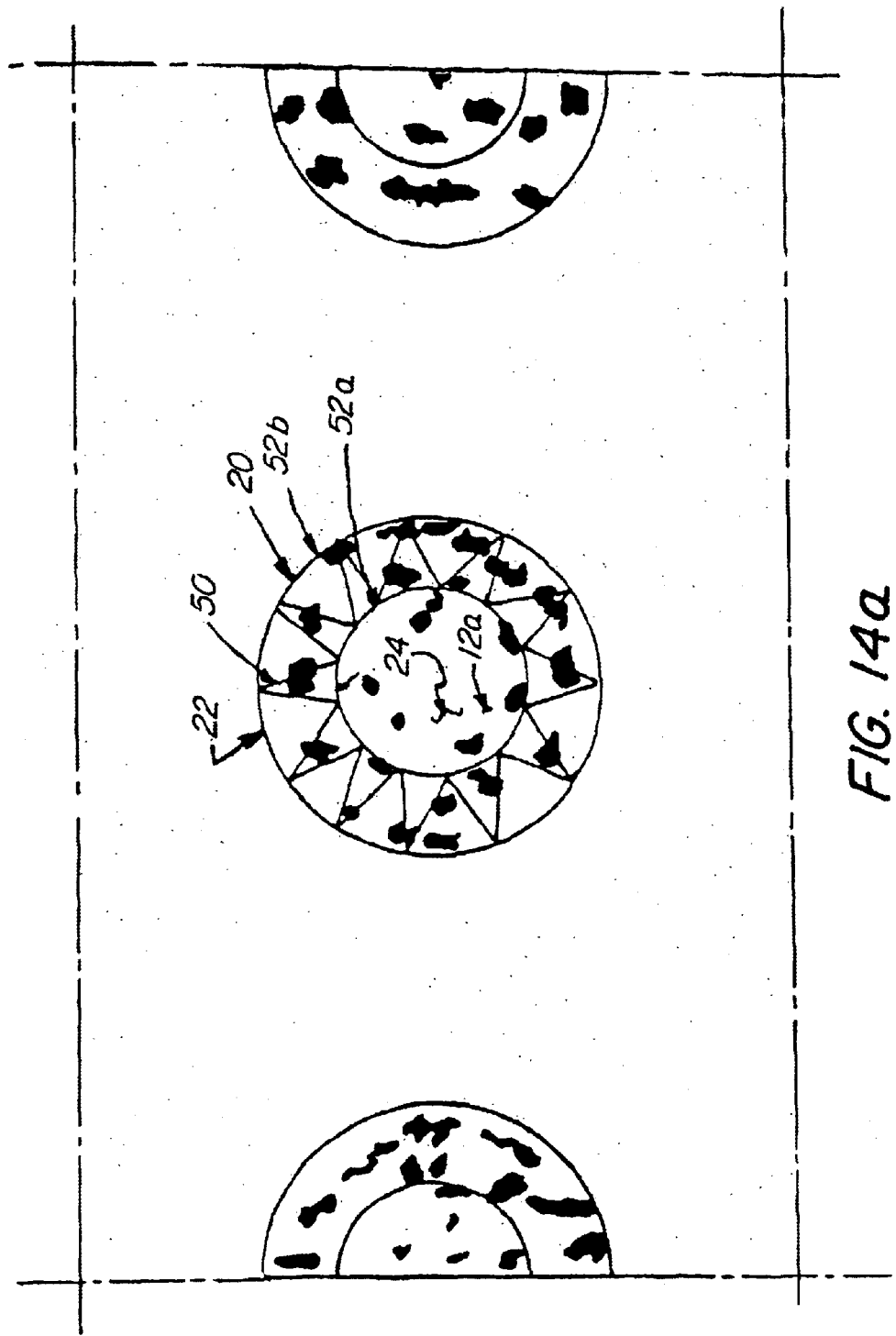
FIGS. 14a and 14b are enlarged views of area A—A of FIG. 1a of a circle sample plate wherein a path, in accordance with one embodiment of the invention, to irradiate crystals produced using CHCA or SA is illustrated.
Figure 14B:
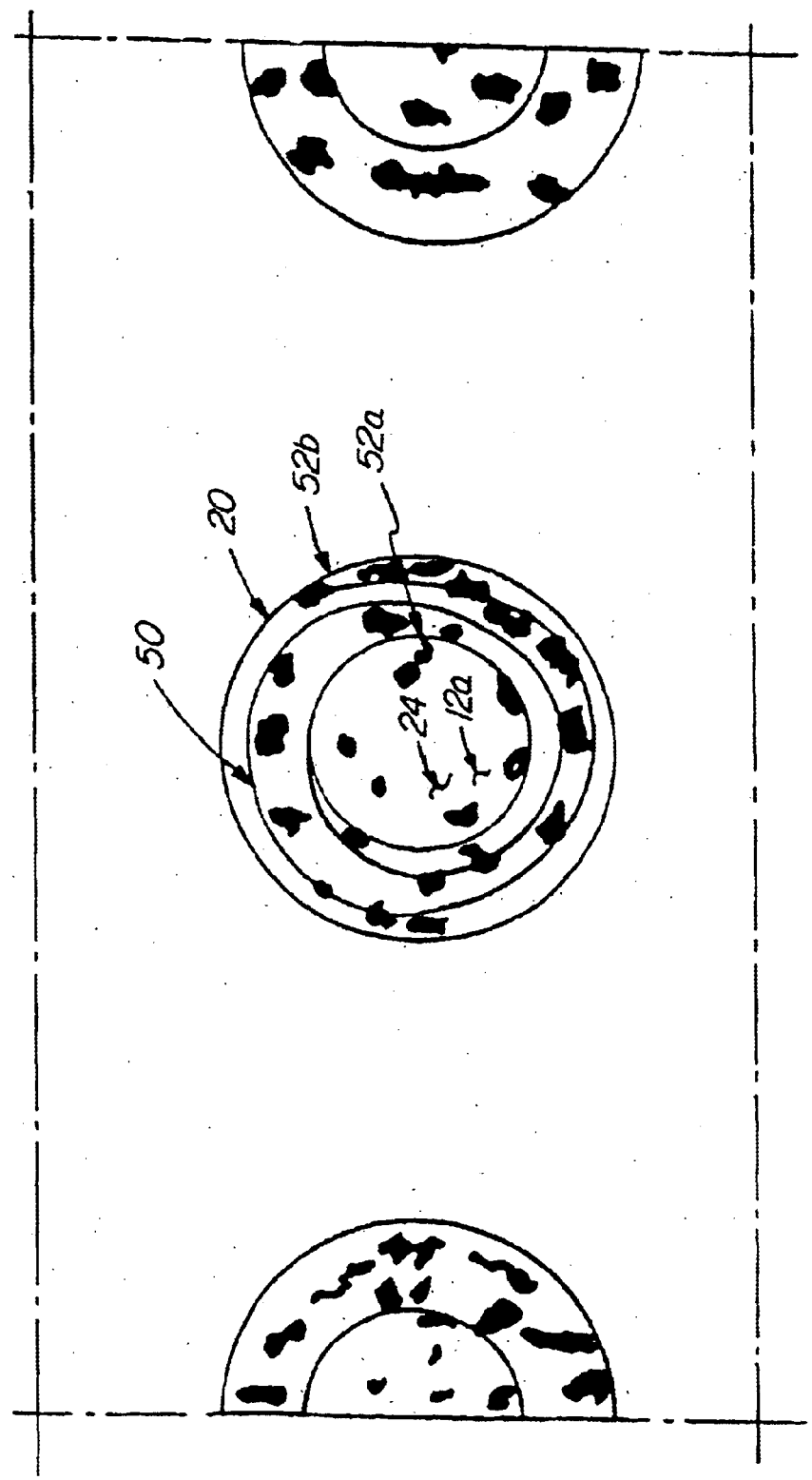

FIGS. 14a and 14b illustrate scanning pattern 50 in accordance with one embodiment of the invention. Pattern 50 may be any variety of patterns, circuit, or other traverse that irradiates crystal 42 efficiently by minimizing the length of the path while maximizing the number of crystals 42 that are irradiated.

FIGS. 14a and 14b are enlarged views of area A—A of FIG. 1 of circle sample plate 10 in accordance with one embodiment of the invention wherein a scanning path to irradiate crystals 42 produced using CHCA or sinapinic acid is illustrated. Laser beam 48 (not shown for clarity) utilizes pattern 50 that is confined by two predetermined boundaries; inner boundary 52a that is approximate with the perimeter of target area 24 and an outer boundary 52b that is within margin 22. Boundaries 52a and 52b may be predetermined according to experience by an operator, statistical sampling, by an algorithm, or any other suitable means.

One embodiment of scanning pattern 50 is illustrated in FIG. 14a. Pattern 50 is a cross-pattern that oscillates between boundary 52a on target area 24 and boundary 52b within sample site 20. Another embodiment is illustrated in FIG. 14b. Therein, pattern 50 is spiral pattern that starts at boundary 52a and in one or more circuits ends at boundary 52b. Other patterns or combinations of patterns may also be used for pattern 50.

For the cross pattern illustrated in FIG. 14a, an algorithm may include the number of oscillations, n, required to cover the area of margin 22 based on a certain confidence level, c, as expressed by a percentage or a ratio. A confidence level of 1 may mean certainty that all crystals 42 have been irradiated. Thus, $$n = (3 \times r_1^2)/r_2^2 \times c \qquad \text{Equation 1}$$

where $r_1$ is the radius of target area 24 and $r_2$ is the effective radius of laser beam 48. Therein, if target area 24 is 1 mm in diameter, laser beam 48 has an effective diameter of 0.1 mm, and a confidence level of 75% is desired, 56.25 oscillation are required if boundaries 52a and 52b are at perimeters of margin 22.

Figure 15A:
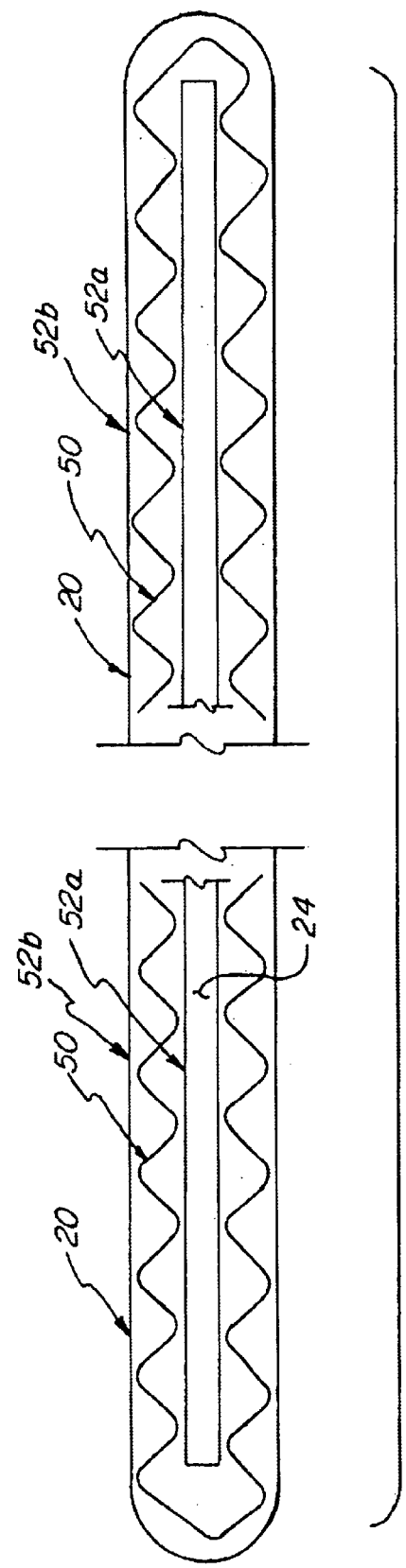
FIGS. 15a and 15b are enlarged views of one sample site of a channel sample plate wherein a path, in accordance with one embodiment of the invention, to irradiate crystals produced using CHCA or SA is illustrated.
Figure 15B:
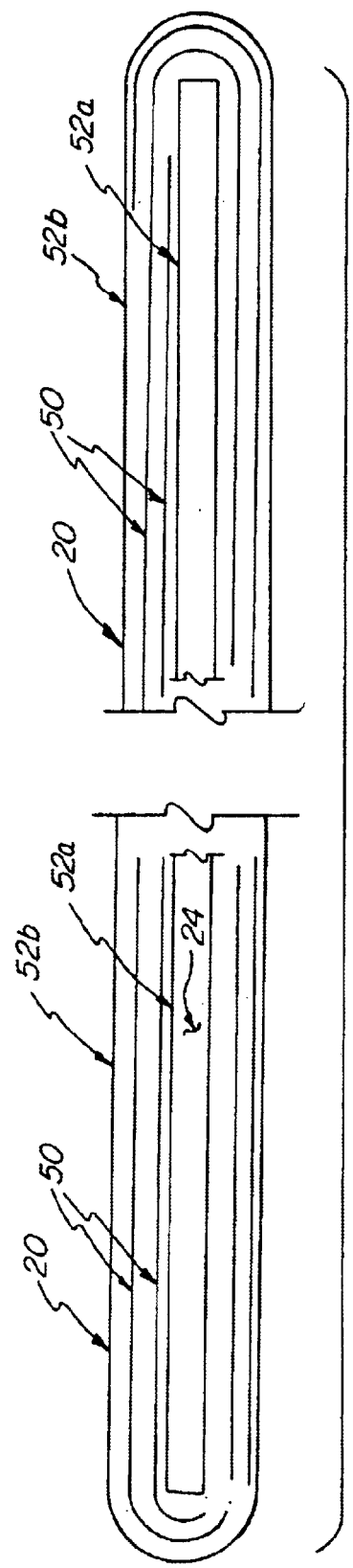

Similarly, pattern 50 may be advantageously employed to more to reduce the time and travel of UV laser and more efficiently irradiate crystals 42 on a channel sample plate. FIGS. 15a and 15b are enlarged views of one sample site of a channel sample plate wherein a scanning pattern, in accordance with one embodiment of the invention, to irradiate crystals produced using CHCA or SA is illustrated.

Therein, similarly, laser beam 48 utilizes pattern 50 that is confined by two predetermined boundaries; inner boundary 52a that is approximate with the perimeter of target area 24 and an outer boundary 52b that is within or coincident with sample site 20. Boundaries 52a and 52b may be predetermined according to experience by an operator, statistical sampling, by an algorithm, and/or any other suitable means. Illustrated in FIG. 15a is a scanning pattern 50 that alternates between boundaries 52a and 52b, and illustrated in FIG. 15b is a path that is a spiral pattern 50. Other patterns may also be used.

In accordance with one embodiment of the invention, specimen 40 is applied on sample plate 10 using the electrospray deposition method. Critical to the electrospray deposition method is that specimen 40 is deposited in a smooth and constant application. Sample plate 10 moves on a platform while a liquid chromatography system elutes specimen 40 using a solvent and specimen 40 is applied by electrospray on sample plate 10 for mass spectrometry analysis.

Sample plate 10 is a channel sample plate or a circle sample plate and cooperatively progresses from one location to another with a liquid chromatography system. In accordance with one embodiment of the invention, sample plate is located on a moving platform that operates at a predetermined speed. Preferably, the platform is operator controllable and adjustable, and further includes one or more check mechanisms to ensure a precise predetermined speed that cooperates with the electrospray deposition.

A liquid chromatography system, such as micro-liquid chromatography system or nano-liquid chromatography system is provided to elute specimen 40 and apply it by electrospray on sample plate 10. Typically, the liquid chromatography system includes a reversed-phase column. The liquid chromatography system is eluted with a matrix of the CHCA formulation at a concentration of 1 mg of CHCA per 1 ml of solvent or SA formulation at a concentration of 1 mg of SA per 1 ml of solvent; although other matrices may also be used. Therein, the percentage of acetonitrile varies from 0% to 70% over the course of eluting specimen 40 from the column during the time period of elution, typically 15 to 60 minutes.

In accordance with one embodiment of the invention, specimen 40 is applied on channel sample plate 10 by direct application of specimen 40 in liquid form such as by streaking. Therein, sample plate 10 moves on a platform while a stationary liquid chromatography system applies specimen 40. Specimen 40 is applied to channel sample plate 10 at a continuous rate over a predetermined length of target area 24, preferably at a rate 1 µl per 1 mm of length of target area 24, while specimen 40 is applied to circle sample plate 10 at a rate consistent with the size of target area 24. Preferably, specimen 40 is applied within sample site 20 that is no more than 0.2 mm from the periphery of target area 24. Specimen 40 then quickly forms crystals 42 that deposit on rough surface 14a from where they are irradiated using a UV laser.

The present novel invention is also contemplated in additional embodiments. In accordance with one embodiment of the invention, sample plate 10 is produced includes sample site 20 wherein mask 14 is selectively applied with rough surface 14a to surface 12a so that mask 14 is surrounded by surface 12a. Specimen 40 may be applied to sample plate 10 using the dried droplet method by spotting, streaking, or spraying or by the electrospray deposition method. Specimen 40 may also be applied by washing or submerging sample plate 10 with or in specimen 40. Crystals 42 will then form on mask 14 in peripheral margin 22 and may be efficiently irradiated using laser beam 48.

What is claimed is:

1. A sample plate for mass spectrometric analysis of a specimen comprising:
   a substrate having an electrically conductive surface;
   a mask disposed upon the substrate to form at least one sample site, wherein said mask has a rougher surface than the substrate, and wherein said sample site comprises a central portion formed from the electrically conductive surface and a marginal portion formed from the mask, the marginal portion more hydrophobic than the central portion.

2. The sample plate of claim 1, wherein the rough surface comprises a mesh having a length and a width selected from a range of 30×30 µm to 500×500 µm.

3. The sample plate of claim 1, wherein the mask comprises polytetrafluoroethylene.

4. The sample plate of claim 1, wherein the rough surface comprises a texture for promoting crystallization of the specimen adjacent the electronically conductive surface.

5. The sample plate of claim 1, wherein the mask comprises a marking agent for producing a predetermined analytical result.

6. The sample plate of claim 1, wherein the electrically conductive surface comprises an electrically conductive coating.

7. The sample plate of claim 6, wherein the electrically conductive coating comprises an electrically conductive polymer coating.

8. The sample plate of claim 1, wherein the substrate comprises a nonconductive material.

9. The sample plate of claim 1, wherein the sample plate has a dimension of a microtiter plate.

10. The sample of claim 1, wherein the sample plate further comprises a reference indicator for archiving the sample plate.

11. The sample plate of claim 10, wherein the reference indicator comprises a surface sensitive to an ultra-violet laser light.

12. A sample plate for mass spectrometric analysis comprising:
    a substrate having an electrically conductive surface; and
    a mask disposed upon the substrate adjacent to the electrically conductive surface, wherein said mask is more hydrophobic than the electrically conductive surface and formulated to promote crystallization of the specimen, and wherein said mask has a rougher surface than the substrate.

13. The sample plate of claim 12, wherein the rougher surface comprises a mesh having a length and a width selected from a range of 30×30 µm to 500×500 µm.

14. The sample plate of claim 12, wherein the mask comprises polytetrafluoroethylene.

15. The sample plate of claim 12, wherein the mask comprises a marking agent for producing a predetermined analytical result.

16. The sample plate of claim 12, wherein the electrically conductive surface comprises an electrically conductive coating.

17. The sample plate of claim 16, wherein the electrically conductive coating comprises an electrically conductive polymer coating.

18. The sample plate of claim 12, wherein the substrate comprises a nonconductive material.

19. The sample plate of claim 12, wherein the sample plate has a dimension of a microtiter plate.

20. The sample plate of claim 12, wherein the mask comprises a synthetic polymer.

21. The sample plate of claim 1, wherein the mask comprises a synthetic polymer.

* * * * *